US010721907B2

(12) United States Patent
Cao et al.

(10) Patent No.: US 10,721,907 B2
(45) Date of Patent: Jul. 28, 2020

(54) ANTIMICROBIAL COMPOSITIONS AND METHODS WITH NOVEL POLYMERIC BINDING SYSTEM

(71) Applicants: Zhengbing Cao, Bothell, WA (US); Xinbo Sun, Bothell, WA (US); Simon Johnston, Bellevue, WA (US); Jeffrey F. Williams, Langley, WA (US)

(72) Inventors: Zhengbing Cao, Bothell, WA (US); Xinbo Sun, Bothell, WA (US); Simon Johnston, Bellevue, WA (US); Jeffrey F. Williams, Langley, WA (US)

(73) Assignee: OXISCIENCE, LLC, Redmond, WA (US)

( * ) Notice: Subject to any disclaimer, the term of this patent is extended or adjusted under 35 U.S.C. 154(b) by 0 days.

(21) Appl. No.: 16/043,469

(22) Filed: Jul. 24, 2018

(65) Prior Publication Data

US 2018/0325076 A1    Nov. 15, 2018

Related U.S. Application Data

(62) Division of application No. 14/838,717, filed on Aug. 28, 2015, now Pat. No. 10,028,482.

(60) Provisional application No. 62/043,151, filed on Aug. 28, 2014.

(51) Int. Cl.
| | | |
|---|---|---|
| *A01K 1/015* | (2006.01) | |
| *A01N 43/50* | (2006.01) | |
| *A61K 31/53* | (2006.01) | |
| *A61K 31/4166* | (2006.01) | |
| *A61L 15/46* | (2006.01) | |
| *A01N 43/66* | (2006.01) | |
| *A01N 59/00* | (2006.01) | |
| *A61L 15/22* | (2006.01) | |
| *A61L 15/28* | (2006.01) | |
| *A61K 31/00* | (2006.01) | |
| *A01N 33/12* | (2006.01) | |

(52) U.S. Cl.
CPC .......... *A01K 1/0154* (2013.01); *A01K 1/0152* (2013.01); *A01K 1/0155* (2013.01); *A01N 33/12* (2013.01); *A01N 43/50* (2013.01); *A01N 43/66* (2013.01); *A01N 59/00* (2013.01); *A61K 31/00* (2013.01); *A61K 31/4166* (2013.01); *A61K 31/53* (2013.01); *A61L 15/22* (2013.01); *A61L 15/28* (2013.01); *A61L 15/46* (2013.01); *A61L 2300/204* (2013.01); *A61L 2300/404* (2013.01); *A61L 2300/606* (2013.01)

(58) Field of Classification Search
CPC ... C07C 231/12; C07C 235/76; C07C 201/12; C07C 253/30; C07C 205/12; C07C 255/50; A01N 59/00; A01N 25/08; A01N 25/22; A01N 25/26; A01N 33/12; A01N 43/50; A01N 43/66; C07D 413/06; C07D 213/04; C07D 513/04; C07F 7/1852; C07F 7/1856; A61K 8/44; A61K 8/585; A61K 8/608; A61K 8/73; A61K 8/86; A61K 8/894; A61K 2039/6037; A61K 39/09; A61K 47/646; A61K 31/00; A61K 31/4166; A61K 31/53; A61K 39/092; A61K 39/095; A61K 47/4833; A61K 47/6415; A61K 47/48261; A61L 15/28; A61L 15/22; A61L 15/46; A61L 2300/204; A61L 2300/404; A61L 2300/606; A61Q 19/00; A01K 1/0152; A01K 1/0154; A01K 1/0155
See application file for complete search history.

(56) References Cited

U.S. PATENT DOCUMENTS

| | | | |
|---|---|---|---|
| 6,770,287 B1 * | 8/2004 | Sun ........................ | A01N 59/00 424/404 |
| 2003/0044377 A1 | 3/2003 | Worley et al. | |
| 2006/0148940 A1 * | 7/2006 | Sun ...................... | C08K 5/0058 524/99 |
| 2009/0324536 A1 | 12/2009 | Sun et al. | |
| 2010/0029797 A1 * | 2/2010 | Worley .................. | A01N 59/00 521/147 |
| 2011/0154557 A1 * | 6/2011 | Gray ...................... | A41D 13/11 2/206 |

OTHER PUBLICATIONS

Cerkez ("N-Halannine Biocidal Coatings via a Layer-by-Layer Assembly Technique", Langmuir, 2011, 27, 4091-4097) (Year: 2011).*
Cerkez, "N-Halamine Biocidal Coatings via a Layer-by-Layer Assembly Technique", Langmuir, 2011, 27, 4091-4097.
International Search Report PCT/US2015/047212.

* cited by examiner

*Primary Examiner* — Audrea B Coniglio
(74) *Attorney, Agent, or Firm* — Alvin Rockhill

(57) ABSTRACT

The present invention includes multifunctional compositions, methods and binding systems to provide disinfecting and deodorizing coatings for hard and soft surfaces, inorganic and organic solid surfaces and particulate media and other related substrates, including human and animal skin and skin lesions; to provide neutralizing functions for malodors generated by both human, animal and industrial fluids and solid wastes; and to provide neutralizing and degrading functions for nuisance and noxious chemicals. The present invention provides compositions and methods for producing disinfecting, oxidizing and enzyme-inhibiting fluids enabling preparation of durable, stable biocidal and deodorizing coatings and media which can be widely used for biological agent control, prevention and elimination of odors, and degradation of noxious agents susceptible to chemical oxidation, and which take forms that are inoffensive to users and offer high convenience.

19 Claims, 3 Drawing Sheets

ANTIMICROBIAL COMPOSITIONS AND METHODS WITH NOVEL POLYMERIC BINDING SYSTEM

This is a divisional of U.S. patent application Ser. No. 14/838,717, filed on Aug. 28, 2015, which claims the benefit of U.S. Provisional Patent Application Ser. No. 62/043,151, filed on Aug. 28, 2014. The teachings of U.S. patent application Ser. No. 14/838,717 and U.S. Provisional Patent Application Ser. No. 62/043,151 are incorporated by reference herein in their entirety.

TECHNICAL FIELD OF THE INVENTION

The present invention relates in general to the field of antimicrobial and deodorizing materials, and more particularly, to compositions and methods to provide the antimicrobial and deodorizing functions for a wide range of applications.

BACKGROUND OF THE INVENTION

Without limiting the scope of the invention, its background is described in connection with antimicrobial and deodorizing compositions, methods and binding systems to provide antimicrobial and deodorizing functional coatings to hard and soft surfaces including textiles, inorganic and organic solid media, particulates, porous and non-porous, and other related subjects, including human and animal skin, and skin lesions; to provide neutralizing function for odors generated by both human and animal fluid and solid wastes, and for the oxidative degradation of noxious agents that contact the functional coatings.

Without limiting the scope of the invention, it is generally based upon and utilized in conjunction with compositions and methods to stabilize N-halamine-based antimicrobial and deodorizing subjects; and to provide the formulas to reduce chlorine odor and gas phase corrosiveness for halogen-based functionally coated subjects.

Without limiting the scope of the invention, the N-halamines can be immobilized onto targeting subjects via polymeric binder with physical and/or chemical bindings with synergism. The interactions include but are not limited to van der Waals interaction, complex combination, ionic interaction, hydrogen bonds, crosslinking, free radical interaction, etc. In other words, the present invention provides compositions and methods for producing disinfecting and deodorizing fluids, biocidal, oxidative coatings and media which can be widely used for biological control, prevention and elimination of odor and other noxious agents, and the inhibition of enzymes that generate malodors from organic substrates. Without limiting the scope of the invention, functional coatings and media can be stable on storage and durable in use. Without limiting the scope of the invention, the discovered halogen stabilizing compositions can provide reduction of chlorine odor emanating from N-halamine-based antimicrobial and deodorizing subjects. Without limiting the scope of the invention, the discovered halogen stabilizing compositions can provide reduction of corrosion caused by halogens from N-halamines. Despite the extensive efforts being made today to prevent the spread of infectious agents, infectious diseases continue to be the third leading cause of death in the United States and worldwide. Healthcare-associated infections (HAIs) continue to be one of the world's most pressing and expensive healthcare problems. Environmental hard and soft surfaces contaminated with infectious agents play an important role in transmission of infections, and they are responsible for about 20% of the documented outbreaks of healthcare-associated infections. Cross-infections are not only the main causes of morbidity and mortality in hospitals, but also they increase hospital stays and costs. The rates of nosocomial infections, especially by those caused by antibiotic resistant bacteria, are increasing alarmingly over the globe.

Although more rigorous infection control measures are being implemented, it is clear that the current modalities to reduce nosocomial infections are not sufficient. One critical factor for transmission of infectious agents is the ability of microorganisms to survive on environmental surfaces. It has been well-established that many infectious agents can survive for a long period of time in the environment. For example, on various hospital surfaces, gram-positive bacteria (vancomycin-sensitive and -resistant Enterococci and methicillin-sensitive and -resistant Staphylococci) survived for at least one day, and some survived for more than 90 days; gram-negative bacteria (including *Pseudomonas aeruginosa, Escherichia coli, Klebsiella pneumoniae, Serratia marcescens, Proteus mirabilis, Acinetobacter species*, and *Enterobacter* species) survived from 2 hours to more than 60 days; medically important fungi (*Candida* spp., *Aspergillus* spp., *Fusarium* spp., *Mucor* spp., and *Paecilomyces* spp.) survived for days to weeks; and viruses (parainfluenza viruses, influenza A and B viruses, respiratory syncytial viruses, human enteric viruses and SARS coronavirus) could survive for hours to days. For example, a hospital outbreak of Methicillin-resistant *Staphylococcus aureus* (MRSA) was directly linked to a stretcher and a handheld shower; a *Pseudomonas aeruginosa* outbreak in a hematology-oncology unit was caused by contaminated surface cleaning equipment; and a norovirus outbreak at a long-term-care facility was associated with contaminated surfaces of case-residents' rooms, dining room tables, and elevator buttons. Recent studies showed that patients harboring multidrug-resistant bacteria such as MRSA and Vancomycin-Resistant Enterococci (VRE) could heavily contaminate their surrounding environment, and the contaminated surfaces could significantly increase the risk of transmission to subsequent occupants.

In response to the wide spreading of infectious pathogens, biofilms and odor, antimicrobial surfaces that can effectively inactivate microorganisms upon contact have attracted considerable research interests. Those methods have been extensively used in the production of woods, papers, plastics, textiles, coatings, etc. The main purpose of adding biocides into polymers, however, is to protect the polymeric materials from deterioration and discoloration caused by microbial attacks.

Recently, the development of antimicrobial surfaces that effectively inactivate pathogens, odor-causing microorganisms and prevent biofilm formation has become an urgent issue, but successful examples are still few and limited in scope. The N-halamines exhibit potent durable antimicrobial properties against microorganisms. Additionally, they can prevent or minimize noxious odors by inactivating upon contact microorganisms, the malodorous products of microbes, and even the enzymes used by microbes that generate malodorous end products, such as those that, through catalytic enzymology, cause the decomposition of organic matter in bodily wastes to ammonia or other noxious materials.

Without limiting the scope of the invention, its background is described in connection with antimicrobial and deodorizing compositions, methods and binding systems to provide antimicrobial and odor and noxious chemical neutralizing functions to coated subjects. Specifically, the present invention provides compositions and methods for providing antimicrobial and odor and noxious chemical control functions for hard and soft surfaces including coatings, textile, inorganic and organic solid media, particulate porous and nonporous subjects, human and animal skin and skin lesions, and other related subjects.

SUMMARY OF THE INVENTION

This invention is based upon the discovery that new multifunctional compositions with halogen stabilizing and/or novel binding and/or targeting systems can be used to add and/or immobilize N-halamine onto a wide range of subjects to provide potent antimicrobial and deodorizing functions. Several customized N-halamine-containing compositions and methods were invented to provide antimicrobial and deodorizing functions with reduced chlorine odor emanations and gas phase corrosiveness for a wide of range of applications.

The present inventions are related to compositions and methods for controlling microbes, and reducing odor in various environmental and biological systems and structures; to compositions and methods for reducing chlorine odor emanations and corrosiveness caused by halogen-based antimicrobial subjects; to compositions and methods to make stable, durable functional coatings for both soft and hard surfaces, inorganic and organic, solid and particulate, porous and nonporous, and including human and animal skin, intact and afflicted with pathological lesions. Several customized polymeric binding systems were invented to immobilize N-halamine onto subjects to provide multifunctional surfaces with antimicrobial, deodorizing, oxidative and enzyme inhibiting functions that can affect malodorous compounds, their generation by microbial metabolism, and the persistence of noxious compounds. Potential applications on hard and soft surfaces include, but are not limited to, textiles, plastic, wood, metal, glass, and marble, minerals, organic materials of plant origin, and mammalian skin. The potential applications in antimicrobial and deodorizing media include, but are not limited to, odor control cat litter, refrigerator deodorizer and other odor-related subjects, including those employed in personal care and pet care.

Without limiting the scope of the invention, the method comprises adding one or more water soluble and/or water dispersible N-halamine compounds, such as, 2-chloro-1,3,5-triazine-2,4,6-triamine, and cationic Quaternary Ammonium Moieties (QAMs)-based N-halamines, etc. The halogen stabilizing agent can be one or more free radical scavengers, such as, hydroquinone, (2,2,6,6-Tetramethylpiperidin-1-yl)oxy, 2,2,6,6-tetramethyl-piperidine-1,4-diol, 2,2,6,6-Tetramethyl-4-piperidinol. The binding ingredients can be one or more water soluble/dispersible natural or synthetic polymers, such as, starch, cellulose, gelatin, etc. and their derivatives, or vinyl or acrylic resin emulsions. The potential media to be coated include, but are not limited to, sand, zeolite, glass beads, clay, corncobs, grass, and wood.

Further embodiments of the current disclosure present a class of novel water soluble cationic Quaternary Ammonium Moieties (QAMs) N-halamines comprising those structures according to formula I to V:

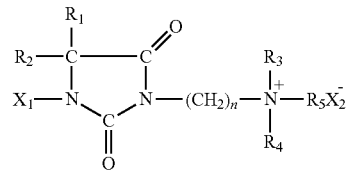

wherein:
$R_1, R_2$ = lower alkyl of 1 to 8 carbons
$R_3, R_4, R_5$ = lower alkyl of 1 to 10 carbons
$X_1, X_2$ = Cl, Br
$n$ = 4 to 12

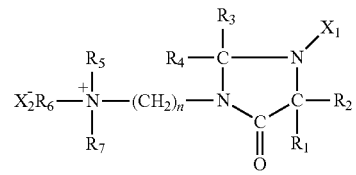

wherein:
$R_1, R_2, R_3, R_4$ = lower alkyl of 1 to 8 carbons
$R_5, R_6, R_7$ = lower alkyl of 1 to 10 carbons
$X_1, X_2$ = Cl, Br
$n$ = 4 to 12

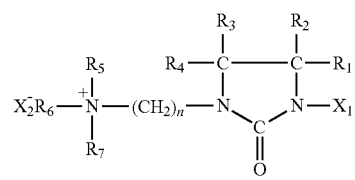

wherein:
$R_1, R_2, R_3, R_4$ = lower alkyl of 1 to 8 carbons
$R_5, R_6, R_7$ = lower alkyl of 1 to 10 carbons
$X_1, X_2$ = Cl, Br
$n$ = 4 to 12

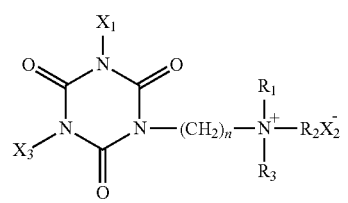

wherein:
$R_1, R_2, R_3$ = lower alkyl of 1 to 8 carbons
$X_1, X_2$ = Cl, Br
$X_3$ = H, Cl, Br
$n$ = 4 to 12

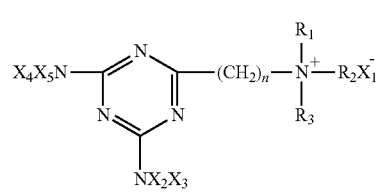

wherein:
$R_1, R_2, R_3$ = lower alkyl of 1 to 8 carbons
$X_1$ = Cl, Br
$X_2, X_3, X_4, X_5$ = H, Cl, Br
$n$ = 4 to 12

The cationic QAMs-based N-halamines contain at least one kind of Quaternary Ammonium Moiety (QAM) that provides desired positive charges, at least one kind of N-halamines that provide biocidal and deodorizing, oxidative function. Further, most of polymeric binders in this invention possess negative charge in solution form and possess negative surface charge in dried film form. The negatively-charged polymers provide strong binding/stabilizing capability for those positively-charged QAMs-based N-halamines.

The subject invention more specifically reveals a water-based disinfecting and deodorizing fluid which is comprised of (a) at least one water soluble/dispersible N-halamine, including but not limited to, N-chloro-N-sodiomethylbenzenesulfonamidate trihydrate, N,N-dichloro-4-methylbenzenesulfonamide, N-bromo-N-sodio-4-nitrobenzenesulfonamidate, N,N-dichlorobenzenesulfonamide, N-chloro-N-sodiobenzenesulfonamidate, mono-chlorosulfamate, dichlorosulfamate, N-chloroimidodisulfonates, sodium N-chloro-N-arylsulfamates, 2,4,6,8-tetrachloro-2,4,6,8-tetrazobicyclooctane-3,7-dione, sodium trichloroimidometaphosphamate, N-halosulfinylamines, N-halo-N-sodioamidates, chloroisocyanurates, N-halocarbamidates, N-halosulfonamidates, N-chloro-imidodisulfonate, N,N-dichloromethylamine, 2-chloro-1,3,5-triazine-2,4,6-triamine, 2,4-dichloro-1,3,5-triazine-2,4,6-triamine, 2,4,6-trichloro-1,3,5-triazine-2,4,6-triamine, 1-chloro-5,5-dimethylhydantoin, 1-bromo-5,5-dimethylhydantoin, 1,3-dibromo-5,5-dimethylhydantoin 1-chloro-3-bromo-5,5-dimethylhydantoin, 1,3-dichloro-5,5-dimethylhydantoin, 1-chloro-4,4,5,5-tetramethylimidazolidin-2-one, 1,3-dichloro-4,4,5,5-tetramethylimidazolidin-2-one, 1-chloro-2,2,5,5-tetramethylimidazolidin-4-one, 1,3-dichloro-2,2,5,5-tetramethylimidazolidin-4-one, 1,3-dichloro-s-triazine-2,4,6-trione, trichloroisocyanuric acid, potassium dichloroisocyanurate, sodium dichloroisocyanurate, potassium dibromoisocyanurate, sodium dibromoisocyanurate, mono to hexachloromelamine, mono to hexabromomelamine, 3-chloro-4,4-dimethyl-2-oxazolidinone, N-chlorosuccinimide, 1-chloropyrrolidine-2,5-dione, 1,3-dichlorotetrahydroquinazoline-2,4-dione, 1,4-dichloro-2,2,5,5-tetrasubstituted-piperazine-3,6-diones, N-chloro-2,2,6,6-tetramethylpiperidine, N-chloro-4-amino-2,2,6,6-tetramethylpiperidine, polymer-bound N-chloro-N-sodiobenzenesulfonamidates, chlorinated polyacrylamide, brominated polyacrylamide, chlorinated poly(methacrylamide), brominated poly(methacrylamide), poly(N-chloro-2,2,6,6-tetramethyl-4-piperidinyl acrylate), poly(N-chloro-hydantoin-methyl-p-styrene) emulsion, 1-chloro-3-bromoalkyltrimethylammonium-4,4,5,5-tetramethyl imidazolidin-2-one, 1-bromo-3-bromoalkyltrimethylammonium-4,4,5,5-tetramethyl imidazolidin-2-one, 1-chloro-3-bromoalkyltrimethylammonium-2,2,5,5-tetramethyl imidazolidin-4-one, 1-bromo-3-bromoalkyltrimethylammonium-2,2,5,5-tetramethyl imidazolidin-4-one, 2-chloro-4-bromoalkyltrimethylammonium-1,3,5-triazine-2,4,6-triamine, 2-bromo-4-bromoalkyltrimethylammonium-1,3,5-triazine-2,4,6-triamine, 1-chloro-3-bromoalkyltrimethylammonium-5,5-dimethylhydantoin, and 1-bromo-3-bromoalkyltrimethylammonium-5,5-dimethylhydantoin; and (b) at least one water soluble halogen stabilizing compound selected from the group consisting of hydroquinone, (2,2,6,6-tetramethylpiperidin-1-yl)oxy, 2,2,6,6-tetramethyl-piperidine-1,4-diol, 2,2,6,6-tetramethyl-4-piperidinol, 4-amino-2,2,6,6-tetramethylpiperidine, 2,2,6,6-tetramethylpiperidine, 2,2,6,6-Tetramethyl-4-piperidyl methacrylate, 2,2,6,6-tetramethyl-4-piperidone, (2,2,6,6-tetramethylpiperidin-4-yl)benzoate, 1,1'-ethylenebis(3,3,5,5-tetramethylpiperazinone), 4-acetamido-2,2,6,6-tetramethyl-piperidine, bis(2,2,6,6-tetramethyl-4-piperidyl) succinate, bis(2,2,6,6-tetramethylpiperidin-4-yl) butanedioate, bis(2,2,6,6-tetramethylpiperidin-4-yl)hexane-1,6-diamine and other water soluble derivatives of 2,2,6,6-tetramethyl piperidine.

The present invention also reveals a water-based disinfecting and deodorizing fluid which is comprised of (a) at least one water soluble/dispersible N-halamine including, but not limited to, N-chloro-N-sodiomethylbenzenesulfonamidate trihydrate, N,N-dichloro-4-methylbenzenesulfonamide, N-bromo-N-sodio-4-nitrobenzenesulfonamidate, N,N-dichlorobenzenesulfonamide, N-chloro-N-sodiobenzenesulfonamidate, mono-chlorosulfamate, dichlorosulfamate, N-chloroimidodisulfonates, sodium N-chloro-N-arylsulfamates, 2,4,6,8-tetrachloro-2,4,6,8-tetrazobicyclooctane-3,7-dione, sodium trichloroimidometaphosphamate, N-halosulfinylamines, N-halo-N-sodioamidates, chloroisocyanurates, N-halocarbamidates, N-halosulfonamidates, N-chloro-imidodisulfonate, N,N-dichloromethylamine, 2-chloro-1,3,5-triazine-2,4,6-triamine, 2,4-dichloro-1,3,5-triazine-2,4,6-triamine, 2,4,6-trichloro-1,3,5-triazine-2,4,6-triamine, 1-chloro-5,5-dimethylhydantoin, 1-bromo-5,5-dimethylhydantoin, 1,3-dibromo-5,5-dimethylhydantoin 1-chloro-3-bromo-5,5-dimethylhydantoin, 1,3-dichloro-5,5-dimethylhydantoin, 1-chloro-4,4,5,5-tetramethylimidazolidin-2-one, 1,3-dichloro-4,4,5,5-tetramethylimidazolidin-2-one, 1-chloro-2,2,5,5-tetramethylimidazolidin-4-one, 1,3-dichloro-2,2,5,5-tetramethylimidazolidin-4-one, 1,3-dichloro-s-triazine-2,4,6-trione, trichloroisocyanuric acid, potassium dichloroisocyanurate, sodium dichloroisocyanurate, potassium dibromoisocyanurate, sodium dibromoisocyanurate, mono to hexachloromelamine, mono to hexabromomelamine, 3-chloro-4,4-dimethyl-2-oxazolidinone, N-chlorosuccinimide, 1-chloropyrrolidine-2,5-dione, 1,3-dichlorotetrahydroquinazoline-2,4-dione, 1,4-dichloro-2,2,5,5-tetrasubstituted-piperazine-3,6-diones, N-chloro-2,2,6,6-tetramethylpiperidine, N-chloro-4-amino-2,2,6,6-tetramethylpiperidine, polymer-bound N-chloro-N-sodiobenzenesulfonamidates, chlorinated polyacrylamide, brominated polyacrylamide, chlorinated poly(methacrylamide), brominated poly(methacrylamide), poly(N-chloro-2,2,6,6-tetramethyl-4-piperidinyl acrylate), poly(N-chloro-hydantoin-methyl-p-styrene) emulsion, 1-chloro-3-bromoalkyltrimethylammonium-4,4,5,5-tetramethyl imidazolidin-2-one, 1-bromo-3-bromoalkyltrimethylammonium-4,4,5,5-tetramethyl imidazolidin-2-one, 1-chloro-3-bromoalkyltrimethylammonium-2,2,5,5-tetramethyl imidazolidin-4-one, 1-bromo-3-bromoalkyltrimethylammonium-2,2,5,5-tetramethyl imidazolidin-4-one, 2-chloro-4-bromoalkyltrimethylammonium-1,3,5-triazine-2,4,6-triamine, 2-bromo-4-bromoalkyltrimethylammonium-1,3,5-triazine-2,4,6-triamine, 1-chloro-3-bromoalkyltrimethylammonium-5,5-dimethylhydantoin, and 1-bromo-3-bromoalkyltrimethylammonium-5,5-dimethylhydantoin; and (c) at least one water soluble/dispersible polymeric binder/stabilizing agent selected from the group consisting of cellulose, carboxylic cellulose, carboxymethyl cellulose, hydroxyethyl cellulose, hydroxypropyl cellulose, starch, guar gum, gelatin, vinyl resin emulsion, acrylic resin emulsion, polyacrylamide, poly(methacrylamide), polyacrylic acid, polyethyleneimine, poly(vinyl alcohol), poly(vinylpyrrolidinone), poly(ethylene glycol), poly(ethylene oxide), poly(N-isopropylacrylamide), poly(2-oxazoline), poly(allylamine hydrochloride), poly(styrenesulfonate), and poly(diallyldimethylammonium chloride).

The subject invention also discloses a water-based disinfecting and deodorizing fluid which is comprised of (a) at least one water soluble/dispersible N-halamine including, but not limited to, N-chloro-N-sodiomethylbenzenesulfonamidate trihydrate, N,N-dichloro-4-methylbenzenesulfonamide, N-bromo-N-sodio-4-nitrobenzenesulfonamidate, N,N-dichlorobenzenesulfonamide, N-chloro-N-sodiobenzenesulfonamidate, mono-chlorosulfamate, dichlorosulfamate, N-chloroimidodisulfonates, sodium N-chloro-N-arylsulfamates, 2,4,6,8-tetrachloro-2,4,6,8-tetrazobicyclooctane-3,7-dione, sodium trichloroimidometaphosphamate, N-halosulfinylamines, N-halo-N-sodioamidates, chloroisocyanurates, N-halocarbamidates, N-halosulfonamidates, N-chloro-imidodisulfonate, N,N-dichloromethylamine, 2-chloro-1,3,5-triazine-2,4,6-triamine, 2,4-dichloro-1,3,5-triazine-2,4,6-triamine, 2,4,6-trichloro-1,3,5-triazine-2,4,6-triamine, 1-chloro-5,5-dimethylhydantoin, 1-bromo-5,5-dimethylhydantoin, 1,3-dibromo-5,5-dimethylhydantoin 1-chloro-3-bromo-5,5-dimethylhydantoin, 1,3-dichloro-5,5-dimethylhydantoin, 1-chloro-4,4,5,5-tetramethylimidazolidin-2-one, 1,3-dichloro-4,4,5,5-tetramethylimidazolidin-2-one, 1-chloro-2,2,5,5-tetramethylimidazolidin-4-one, 1,3-dichloro-2,2,5,5-tetramethylimidazolidin-4-one, 1,3-dichloro-s-triazine-2,4,6-trione, trichloroisocyanuric acid, potassium dichloroisocyanurate, sodium dichloroisocyanurate, potassium dibromoisocyanurate, sodium dibromoisocyanurate, mono to hexachloromelamine, mono to hexabromomelamine, 3-chloro-4,4-dimethyl-2-oxazolidinone, N-chlorosuccinimide, 1-chloropyrrolidine-2,5-dione, 1,3-dichlorotetrahydroquinazoline-2,4-dione, 1,4-dichloro-2,2,5,5-tetrasubstituted-piperazine-3,6-diones, N-chloro-2,2,6,6-tetramethylpiperidine, N-chloro-4-amino-2,2,6,6-tetramethylpiperidine, polymer-bound N-chloro-N-sodiobenzenesulfonamidates, chlorinated polyacrylamide, brominated polyacrylamide, chlorinated poly(methacrylamide), brominated poly(methacrylamide), poly(N-chloro-2,2,6,6-tetramethyl-4-piperidinyl acrylate), poly(N-chloro-hydantoin-methyl-p-styrene) emulsion, 1-chloro-3-bromoalkyltrimethylammonium-4,4,5,5-tetramethyl imidazolidin-2-one, 1-bromo-3-bromoalkyltrimethylammonium-4,4,5,5-tetramethyl imidazolidin-2-one, 1-chloro-3-bromoalkyltrimethylammonium-2,2,5,5-tetramethyl imidazolidin-4-one, 1-bromo-3-bromoalkyltrimethylammonium-2,2,5,5-tetramethyl imidazolidin-4-one, 2-chloro-4-bromoalkyltrimethylammonium-1,3,5-triazine-2,4,6-triamine, 2-bromo-4-bromoalkyltrimethylammonium-1,3,5-triazine-2,4,6-triamine, 1-chloro-3-bromoalkyltrimethylammonium-5,5-dimethylhydantoin, and 1-bromo-3-bromoalkyltrimethylammonium-5,5-dimethylhydantoin; (b) at least one water soluble halogen stabilizing compound selected from the group consisting of hydroquinone, (2,2,6,6-tetramethylpiperidin-1-yl)oxy, 2,2,6,6-tetramethyl-piperidine-1,4-diol, 2,2,6,6-tetramethyl-4-piperidinol, 4-amino-2,2,6,6-tetramethylpiperidine, 2,2,6,6-tetramethylpiperidine, 2,2,6,6-Tetramethyl-4-piperidyl methacrylate, 2,2,6,6-tetramethyl-4-piperidone, (2,2,6,6-tetramethylpiperidin-4-yl)benzoate, 1,1'-ethylenebis(3,3,5,5-tetramethylpiperazinone), 4-acetamido-2,2,6,6-tetramethylpiperidine, bis(2,2,6,6-tetramethyl-4-piperidyl) succinate, bis(2,2,6,6-tetramethylpiperidin-4-yl) butanedioate, bis(2,2,6,6-tetramethylpiperidin-4-yl)hexane-1,6-diamine and other water soluble derivatives of 2,2,6,6-tetramethyl piperidine; and (c) at least one water soluble/dispersible polymeric binder/stabilizing agent selected from the group consisting of cellulose, carboxylic cellulose, carboxymethyl cellulose, hydroxyethyl cellulose, hydroxypropyl cellulose, starch, guar gum, gelatin, vinyl resin emulsion, acrylic resin emulsion, polyacrylamide, poly(methacrylamide), polyacrylic acid, polyethyleneimine, poly(vinyl alcohol), poly(vinylpyrrolidinone), poly(ethylene glycol), poly(ethylene oxide), poly(N-isopropylacrylamide), poly(2-oxazoline), poly(allylamine hydrochloride), poly(styrenesulfonate), and poly(diallyldimethylammonium chloride).

The water-based disinfecting and deodorizing fluid of this invention can be used with other similar products to augment and complement antimicrobial and odor control activities; the formulation can be used to form a co-treatment with major disinfecting and/or deodorizing products including, but not limited to, quaternary ammonium compounds, oxidizers including bleach, phenols including triclosan, alcohols, amides, aldehydes, biocides, baking soda, metals including silver, copper and zinc and their alloys and antimicrobial peptides.

The polymeric binder in the water-based disinfecting and deodorizing fluid of this invention immobilizes the N-halamine via physical and/or chemical interactions after the water-based disinfecting and deodorizing fluid is applied to the surface of a substrate and allowed to dry thereby reducing the odor of free halogen emanating from the dry coating. The polymeric binder in the water-based disinfecting and deodorizing fluid of this invention can also stabilize the N-halamine via physical and/or chemical interactions thereby reducing the odor of free halogen emanating from the dry coating.

In one embodiment of this invention the N-halamine is a cationic N-halamine alkyl which includes aliphatic hydrocarbon chains containing from 2 to 12 carbon atoms, and the water-based disinfecting and deodorizing fluid inactivates microbes including germs which are customarily susceptible to inactivation with halogens. In another embodiment of this invention the disinfecting and deodorizing fluid inactivates microbes that generate odors and inactivates odoriferous chemical agents and other noxious compounds. In a further embodiment of this invention the disinfecting and deodorizing fluid inactivates enzymes dependent on sulfur-containing amino acid residues that catalyze the production of odoriferous chemical agents from natural substrates.

The present invention also reveals a method for preparing an antimicrobial and/or deodorizing and/or enzyme inactivating textile material by applying water-based disinfecting and deodorizing fluid of this invention to a woven or nonwoven textile substrate and allowing the fluid to dry on said substrate to create the antimicrobial and/or deodorizing and/or enzyme inactivating textile material.

The subject invention further discloses a method for preparing an antimicrobial and/or deodorizing and/or enzyme inactivating solid material by applying water-based disinfecting and deodorizing fluid of this invention to a solid substrate and allowing the fluid to dry on said substrate to create the antimicrobial and/or odor and/or enzyme inactivating solid material.

The present invention also reveals a method for preparing an antimicrobial and/or deodorizing and/or enzyme inactivating particulate material by applying water-based disinfecting and deodorizing fluid of this invention to a solid substrate and allowing the fluid to dry on said substrate to create the antimicrobial and/or deodorizing and/or enzyme inactivating solid material, wherein the particulate material is inorganic or organic, porous or non-porous, and natural or synthetic.

The subject invention also reveals a method for disinfecting and/or deodorizing an area of skin on a human or an animal which comprises applying the water-based disinfecting and deodorizing fluid this invention to the area of skin on the human or the animal. The present invention further discloses a method for disinfecting and/or deodorizing a wound on a human or an animal which comprises applying a soft dressing that has been treated with the water-based disinfecting and deodorizing fluid of this invention. The subject invention also reveals a personal hygiene product in the form of a dry powder which has been treated with the water-based disinfecting and deodorizing fluid of this invention.

The present invention also reveals a method for disinfecting and/or deodorizing the surface of equipment for use in food processing, agricultural, or industrial processes which comprises applying the water-based disinfecting and deodorizing fluid of this invention to the surface of the equipment.

This invention also discloses an animal litter which is comprised of a particulate material which has been treated with the antimicrobial and/or deodorizing and/or enzyme inactivating particulate material of this invention. In one embodiment of this invention the animal litter is used for controlling the odor of an animal litter bed, such as a cat litter box, which comprises spreading the animal litter of this invention onto conventional litter as the top layer of litter in the animal litter bed. In such a case the animal litter of this invention will typically be applied as a top layer which is 0.25 inch to about 1 inch thick. The top layer of the animal litter of this invention will more typically be applied as a layer which is 0.25 inch to 0.5 inch thick. The animal litter of this invention can further be comprised of a water activated inorganic or organic particulate component which provides the animal litter with a clumping functionality.

The present invention further reveals an animal litter composition which is comprised of zeolite, a clumping agent and an N-halamine, wherein the clumping agent is present at a level which is within the range of 20 weight percent to 40 weight percent, and wherein the N-halamine is present at a level which is within the range of 0.1 weight percent to 10 weight percent. Such animal letter compositions will typically contain at least 50 weight percent of the zeolite as an inorganic particulate material and can additionally contain additional inert materials which do not interfere with the functionality of the animal letter, such as colorants or pigments. In most cases such animal litter will include the zeolite at a level of at least 55 weight percent and more typically at a level of at least about 60 weight percent. For example, the animal litter can contain from about 55 weight percent to about 65 weight percent of the zeolite, from about 25 weight percent to about 35 weight percent of the clumping agent, and from about 0.1 to 10 weight percent of the N-halomine. It is generally preferred for the animal litter composition to contain from about 60 weight percent to about 65 weight percent of the zeolite, from about 30 weight percent to about 35 weight percent of the clumping agent, and from about 0.2 to 5 weight percent of the N-halomine. Some representative examples of clumping agent which can be used include sodium bentonite, cellulose, guar gum, chitosan, *psyllium*, agar, algin, starch, carrageenan, gum arabic, gum ghatti, gum tragacanth, karaya gum, larch gum, locust bean gum, pectin, quince seed gum, tamarind gum or xanthan gum or a combination of one or more of these compounds.

The present invention also reveals an animal litter composition which is comprised of an inorganic particulate material, a polymeric binder and an N-halamine, wherein the binder is present at a level which is within the range of 0.05 weight percent to 1.0 weight percent, and wherein the N-halamine is present at a level which is within the range of 0.1 weight percent to 10 weight percent. In such animal letter compositions the inorganic particulate matter will typically be present at a level of at least 55 weight percent and will more typically be present at a level of at least 60 weight percent, at least 65 weight percent, at least 70 weight percent, at least 80 weight percent, at least 90 weight percent, at least 95 weight percent, at least 98 weight percent, or at least 99 weight percent. Such animal litter compositions can optionally further contain a clumping agent. For instance, it is particularly advantageous for animal litter compositions which utilized a zeolite as the inorganic particulate material to further contain a clumping agent. Some representative examples of clumping agent which can be used include sodium bentonite, cellulose, guar gum, chitosan, *psyllium*, agar, algin, starch, carrageenan, gum arabic, gum ghatti, gum tragacanth, karaya gum, larch gum, locust bean gum, pectin, quince seed gum, tamarind gum or xanthan gum or a combination of one or more of these compounds. In such animal letter compositions the inorganic will typically be present at a level of at least 55 weight percent and will more typically be present at a level of at least 60 weight percent, at least 65 weight percent, or even more than 70 weight percent.

DETAILED DESCRIPTION OF THE INVENTION

Figure 1:
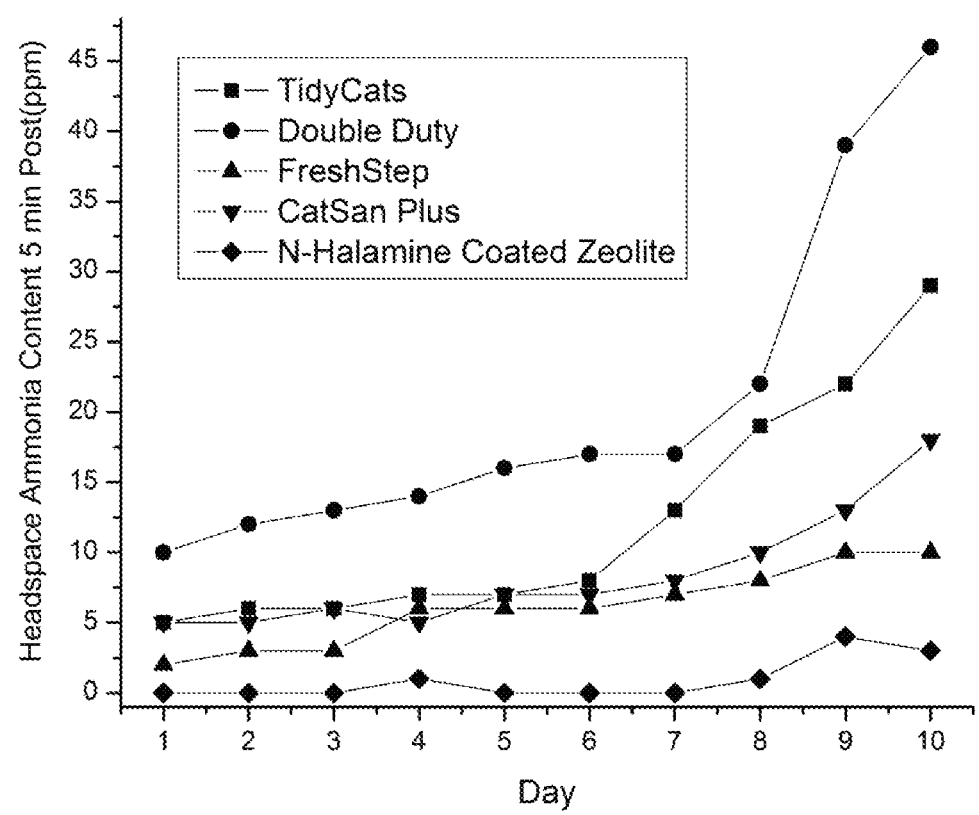
FIG. 1 is a graph showing immediate headspace ammonia content over litter samples spiked with ammonia solution daily to simulate the total urinary output of one cat per day in a worst case scenario in which all the urea in the urine is converted to ammonia.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

N-halamines are compounds in which oxidative halogen is attached to nitrogen. N-halamines release less free halogen than aqueous chlorine species, resulting in increased compatibility with organic materials. N-halamines will be less aggressive toward metal parts than other halogen donors. N-halamines have potent antimicrobial effects against a broad range of microbial agents with low risk of inducing microbial resistance. Otherwise, N-halamines have potent neutralizing effects against a broad range of odor-related molecules, like as hydrogen sulfide, mercaptans, alkyl sulfides, etc. N-halamine structures are capable of converting sulfides to sulfoxides and sulfones, mercaptans to hydrocarbon disulfides and then to sulfoxides and sulfones, alcohols/aldehydes to ketones and then to carboxylic acids, and cyanides to carbon dioxide and ammonium in water, so that malodorous and noxious molecules can be turned into non odorous, hazard-free derivatives.

Various embodiments of the present disclosure provide water soluble cationic N-halamines with QAMs that are capable of providing microorganism-targeting and biofilm-targeting biocidal function. Surface charge and hydrophobicity of both microorganism and a conditioning surface play an important role in microbial attachment on the surface. These two factors have an impact on the length of time cells are associated with the substratum. Surface charge results in electrostatic interaction between two surfaces. In most of the environments, the microorganisms have a net negative charge. Specifically, most bacteria are negatively charged, bacterial cells have a net negative charge on the cell wall, although the magnitude of this charge varies from strain to strain. The surface charges are undoubtedly as complex as those on bacterial cells, and bacterial attachment is related to the interaction of these surface charges. In Gram positive bacteria, the reason for the negative charge is the presence of teichoic acids linked to either the peptidoglycan or to the underlying plasma membrane. These teichoic acids are negatively charged because of presence of phosphate in their structure.

The Gram negative bacteria have an outer covering of phospholipids and Lipopolysaccharides. The lipopolysaccharides impart a strongly negative charge to surface of gram negative bacterial cells. Cationic QAMs-based N-halamines can be used as a biological-targeting biocide for a wide range of biological control applications include but are not limited to soft and hard surfaces and industrial aqueous systems. Biofilm is a sticky, viscous negatively charged substance similar to "bacterial slime", composed of mucopolysaccharides and DNA. Because negative charges are often associated with the biofilm matrix, cationic QAMs-based N-halamines can be used as a biofilm-targeting biocide for a wide range of biofilm control applications include but are not limited to medical device and industrial aqueous systems. One of the best-known of these biofilm-specific properties is the development of antibiotic resistance that can be up to 1,000-fold greater than for planktonic cells. Regular added biocides can effectively inactivate planktonic cells, but may not help to remove biofilm. With industrial aqueous systems where biological and biofilm control is needed, the added positively-charged N-halamine molecules are targeted at microorganisms in the water and biofilms on the equipment surfaces with limited N-halamine content. The positively-charged N-halamines are selectively attracted and immobilized to the biofilm surfaces and then the highly enriched N-halamines in the biofilm will destroy the matrix and inactivate bacteria inside of the biofilm. Biofilms have been found to be involved in a wide variety of microbial infections, by one estimate 80% of all infections. With medical applications in treatment of infections on device surfaces that are colonized by pathogenic microorganisms, this novel biofilm-targeting cationic QAMs-based N-halamines will provide potent biocidal function.

Some water soluble N-halamines, such as 1-chloro-3-bromo-5,5-dimethylhydantoin and 1,3-dichloro-5,5-dimethylhydantoin, are halogenated hydantoins and are effective at inactivating microorganisms in recreational, waste, process waters and preventing biofilm formation on all sorts of surfaces. But those chemicals have strong chlorine odor and limited active life in aqueous systems. Their vapor phase can be corrosive to system components. Although, the chlorine odor and evaporation tendency of partially-halogenated N-halamines can be much lower than that of fully-halogenated ones, the chlorine odor and gas phase corrosiveness are still big concerns and limit their user-acceptance and applications. In principle, there are three types of N-halamine structures possible: imide, amide, and amine. Their stabilities toward dissociation of the N-halogen moieties are in the order amine>amide>imide halamine. The reaction of general N-halamine with water will give the amine, amide, or imide and hypochlorous acid or hypobromous acid. Usually, the inherent chlorine odors come from a trace of chlorine gas which is produced by hypochlorous acid decomposition. Their inherent chlorine odors in aqueous solution vary in the order amine<amide<imide. However, the trace of chlorine gas will generate a light chlorine smell. Bromine-based N-halamines only have the potential to produce hypobromous acid in aqueous solution, and then produce bromine which is liquid and odorless. However, bromine-based aqueous N-halamines show similar chlorine odor in aqueous solution. Those results indicate that the chlorine odors from N-halamine aqueous solution have complicated sources, with part of the chlorine odors attributed to halogenated impurities. Ammonium is a hydrolysis byproduct of some N-halamines. Organic substances are another major source of impurities. Once they contact N-halamines in aqueous solution, the impurities have the potential to release chemicals with objectionable smells, such as chloramines from ammonium and halogenated hydrocarbons from organic substances, some of which are objectionable and toxic.

A halogen stabilizer can be selected from the group consisting of compounds having at least one free radical scavenging moiety capable of reacting with a halogen free radical to stop the formation of halogenated impurities. Those halogen stabilizers can provide extra benefits for N-halamines in aqueous systems, such as, extended shelf-life, improved functional durability, reduced chlorine odor, reduced gas phase corrosiveness and reduced toxicity.

The polymeric binding agents provide a glue-like function to provide durable antimicrobial efficacy once the aqueous formulation is applied onto the surfaces of the substrate. However, those binding polymers also act as secondary stabilizing agents for N-halamines in aqueous systems. Those high molecular weight polymers can be dissolved or dispersed in water to form a well-distributed 3D network or uniform microsphere suspension. Those stretched polymer chains or massive dispersed microspheres provide huge affinitive landing sites and surface areas to allow N-halamine molecules to anchor onto them. The interactions between binding polymer affinitive groups/surfaces with N-halamine molecules include but are not limited to van der Waals interaction, complex combination, ionic interaction, hydrogen bonds, crosslinking, free radical interaction, etc. Once the equilibrium is established, those anchored or bound N-halamines have less potential to release chlorine gas, cause smelly impurities or create toxic substances. The synergistic functions of binding agents in the N-halamines aqueous systems can extend their shelf-life, reduce chlorine odor, reduce gas phase corrosiveness and reduce toxicity.

According to various embodiments, the current invention comprises adding one or more water soluble/dispersible N-halamine compounds including, but not limited to, N-chloro-N-sodiomethylbenzenesulfonamidate trihydrate, N,N-dichloro-4-methylbenzenesulfonamide, N-bromo-N-sodio-4-nitrobenzenesulfonamidate, N,N-dichlorobenzenesulfonamide, N-chloro-N-sodiobenzenesulfonamidate, mono-chlorosulfamate, dichlorosulfamate, N-chloroimidodisulfonates, Sodium N-chloro-N-arylsulfamates, 2,4,6,8-tetrachloro-2,4,6,8-tetrazobicyclooctane-3,7-dione, sodium trichloroimidometaphosphamate, N-halosulfinylamines, N-halo-N-sodioamidates, chloroisocyanurates, N-halocarbamidates, N-halosulfonamidates, N-chloro-imidodisulfonate, N,N-dichloromethylamine, 2-chloro-1,3,5-triazine-2,4,6-triamine, 2,4-dichloro-1,3,5-triazine-2,4,6-triamine, 2,4,6-trichloro-1,3,5-triazine-2,4,6-triamine, 1-chloro-5,5-dimethylhydantoin, 1-bromo-5,5-dimethylhydantoin, 1,3-dibromo-5,5-dimethylhydantoin 1-chloro-3-bromo-5,5-dimethylhydantoin, 1,3-dichloro-5,5-dimethylhydantoin, 1-chloro-4,4,5,5-tetramethylimidazolidin-2-one, 1,3-dichloro-4,4,5,5-tetramethylimidazolidin-2-one, 1-chloro-2,2,5,5-tetramethylimidazolidin-4-one, 1,3-dichloro-2,2,5,5-tetramethylimidazolidin-4-one, 1,3-dichloro-s-triazine-2,4,6-trione, trichloroisocyanuric acid, potassium dichloroisocyanurate, sodium dichloroisocyanurate, potassium dibromoisocyanurate, sodium dibromoisocyanurate, mono to hexachloromelamine, mono to hexabromomelamine, 3-chloro-4,4-dimethyl-2-oxazolidinone, N-chlorosuccinimide, 1-chloropyrrolidine-2,5-dione, 1,3-dichlorotetrahydroquinazoline-2,4-dione, 1,4-dichloro-2,2,5,5-tetrasubstituted-piperazine-3,6-diones,N-chloro-2 2 6 6-tetramethylpiperidine, N-chloro-4-amino-2,2,6,6-tetramethylpiperidine. Any water soluble/dispersible polymeric N-halamines, such as polymer-bound N-chloro-N-sodiobenzenesulfonamidates, chlorinated polyacrylamide, brominated polyacrylamide, chlorinated poly(methacrylamide), brominated poly(methacrylamide), poly(N-chloro-2,2,6,6-tetramethyl-4-piperidinyl) acrylate), poly(N-chloro-hydantoin-methyl-p-styrene) emulsion. Cationic N-halamines, such as 1-chloro-3-bromoalkyltrimethylammonium-4,4,5,5-tetramethyl imidazolidin-2-one, 1-bromo-3-bromoalkyltrimethylammonium-4,4,5,5-tetramethyl imidazolidin-2-one, 1-chloro-3-bromoalkyltrimethylammonium-2,2,5,5-tetramethyl imidazolidin-4-one, 1-bromo-3-bromoalkyltrimethylammonium-2,2,5,5-tetramethyl imidazolidin-4-one, 2-chloro-4-bromoalkyltrimethylammonium-1,3,5-triazine-2,4,6-triamine, 2-bromo-4-bromoalkyltrimethylammonium-1,3,5-triazine-2,4,6-triamine, 1-chloro-3-bromoalkyltrimethylammonium-5,5-dimethylhydantoin, and 1-bromo-3-bromoalkyltrimethylammonium-5,5-dimethylhydantoin, etc. The alkyl can be lower alkyl of 4 to 12 carbons.

Various embodiments of this invention comprise adding one or more water soluble halogen stabilizing compounds including, but not limited to, hydroquinone, (2,2,6,6-tetramethylpiperidin-1-yl)oxy, 2,2,6,6-tetramethyl-piperidine-1,4-diol, 2,2,6,6-tetramethyl-4-piperidinol, 4-amino-2,2,6,6-tetramethylpiperidine, 2,2,6,6-tetramethylpiperidine, 2,2,6,6-tetramethyl-4-piperidyl methacrylate, 2,2,6,6-tetramethyl-4-piperidone, (2,2,6,6-tetramethylpiperidin-4-yl)benzoate, 1,1'-ethylenebis(3,3,5,5-tetramethylpiperazinone), 4-acetamido-2,2,6,6-tetramethylpiperidine, bis(2,2,6,6-tetramethyl-4-piperidyl) succinate, bis(2,2,6,6-tetramethylpiperidin-4-yl) butanedioate, bis(2,2,6,6-tetramethylpiperidin-4-yl)hexane-1,6-diamine and other water soluble derivatives of 2,2,6,6-tetramethyl piperidine, and 2,2,5,5-tetramethylimidazolidin-4-one.

The N-halamine will typically be present in the fluids of this invention at a level which is within the range of 100 ppm to 10 weight percent, will more typically be present at a level within the range of 0.01 to 2 weight percent, and will most typically be present at a level which is within the range of 0.1 to 1 weight percent. The halogen stabilizing compound will typically be present in the fluids of this invention at a level which is within the range of 0.1 to 2 weight percent, and will more typically be present at a level within the range of 0.2 to 0.5 weight percent. The polymeric binder will typically be present in the fluids of this invention at a level which is within the range of 0.1 to 2 weight percent, and will more typically be present at a level within the range of 0.2 to 0.5 weight percent.

According to various embodiments, the current invention comprises adding one or more water soluble/dispersible polymeric binding/stabilizing compounds including, but not limited to, cellulose, carboxylic cellulose, carboxymethyl cellulose, hydroxyethyl cellulose, hydroxypropyl cellulose, starch, guar gum, gelatin, vinyl resin emulsion, acrylic resin emulsion, polyacrylamide, poly(methacrylamide), polyacrylic acid, polyethyleneimine, poly(vinyl alcohol), poly(vinylpyrrolidinone), poly(ethylene glycol), poly(ethylene oxide), poly(N-isopropylacrylamide), poly(2-oxazoline), poly(allylamine hydrochloride), poly(styrenesulfonate), poly(diallyldimethylammonium chloride), etc.

In the most basic form of this invention, it provides a composition and method for preparing stabilized N-halamine-based aqueous disinfecting and deodorizing fluid. One or more water soluble/dispersible N-halamines, such as but not limited to 1-chloro-4,4,5,5-tetramethylimidazolidin-2-one, 1-chloro-2,2,5,5-tetramethylimidazolidin-4-one, 2-chloro-1,3,5-triazine-2,4,6-triamine, N-chloro-2,2,6,6-tetramethylpiperidine, N-chloro-4-amino-2,2,6,6-tetramethylpiperidine, 1-chloro-5,5-dimethylhydantoin and/or 1-bromo-5,5-dimethylhydantoin, and cationic N-halamines, 1-chloro-3-bromoalkyltrimethylammonium-5,5-dimethylhydantoin, 1-bromo-3-bromoalkyltrimethylammonium-5,5-dimethylhydantoin are added into a polymer solution which contains one or more water soluble/dispersible polymeric binders, and one or more water soluble halogen stabilizing agent with or without a wetting agent. The resulting disinfectant solution kills 99.9% of bacteria, fungi, viruses and spores in seconds to minutes, and degrades by oxidation malodorous or noxious compounds in seconds to minutes. Via wiping or spraying, the functional fluid can be used on any commonly touched surfaces to provide persistent protection against contamination for up to days to months. The polymeric binding/stabilizing material is one or more selected from the group consisting of water soluble/dispersible polymers. The preferred polymers are hydroxyethyl cellulose and acrylic resin emulsion. The biocidal compound is one or more selected from the group consisting of water soluble/dispersible N-halamines described above. The preferred biocidal compounds are water soluble mono-halogenated N-halamines. Mono-halogenated N-halamines have less potential to release free halogen than di or multi-halogenated molecules, resulting in increased compatibility and stability. Mono-halogenated N-halamines are also less corrosive toward substrates than other halogen donors. Another class of preferred novel biocidal compounds is water soluble cationic QAMs-based N-halamines which are described in this invention.

The invention pertains to biocidal compounds and methods that can be applied to a wide range of substrates to provide broad-spectrum biocidal activity and potent neutralizing properties against odor-causing microorganisms and noxious chemical agents. In some embodiments, the invention provides antimicrobial function for hard and soft surfaces including coating, textiles, inorganic and organic media, and other related solid and particulate subjects. In some instances, the invention provides neutralizing function for odors generated by both human and animal fluid and solid wastes. The invention provides functional surfaces for oxidative degradation of toxic agents, such as pesticides and for toxic agents used in chemical warfare, or commonly present in industrial fluids such as hydrogen sulfide.

To better expatiate the current invention, five groups will be interpreted based on specific applications.

Group 1: Disinfecting Fluid

According to various embodiments of the invention, the invention provides a process for the making of a disinfecting fluid. The disinfecting fluid can deactivate most common pathogens including bacteria, drug-resistant bacteria, fungi, virus and spores in seconds to minutes. Without limiting the scope of the invention, according to one embodiment of the invention, the disinfecting fluid can be applied onto targeted surfaces via spraying or wiping.

Surfaces can be contaminated when an infected person coughs or sneezes into his or her hands and then touches them. Infectious agents have strong abilities to survive, and some pathogens can survive for up to 90 days in the environment. Spores can remain viable in the environment for periods of months or even years. People can become exposed by touching contaminated surfaces and then their eyes, mouth, or nose before they clean their hands. People getting medical care can catch serious infections called healthcare-associated infections (HAIs). Wide spread HAIs are increasingly associated with multidrug-resistant pathogens including methicillin-resistant *Staphylococcus aureus* (MRSA) and vancomycin-resistant *Enterococcus* (VRE), causing an estimated 88,000 deaths and $4.5 billion in excess healthcare cost in the United States annually. Lately, multidrug-resistant species have also spread out of healthcare facilities, and MRSA infections have been reported in public sites, posing an increasing risk for the general public. Environmental sources contaminated with these microorganisms play a very important role in cross-contamination and cross-infection, and they are responsible for about 20% of the documented outbreaks of HAIs.

*Clostridium difficile*, also known as CDF/cdf, or C. diff, is a species of Gram-positive spore-forming bacteria that is best known for causing antibiotic-associated diarrhea (AAD), was selected to represent spore strains. HAIs are caused by the germ C. diff at historically high levels and are growing problems in healthcare facilities. Outbreaks occur when humans accidentally ingest spores in a medical facility. During the past decade, the emergence of an epidemic C. diff strain has been associated with large outbreaks of C. diff infection (CDI) in North America and Europe. The infection kills 14,000 people a year in America alone. These outbreaks have posed enormous challenges for infection control programs in hospitals and long-term care facilities. Successful control of outbreaks has often required years of effort and sequential implementation of multiple control measures, including antibiotic restriction. C. diff spores are resistant to most routine surface cleaning methods (except for diluted bleach).

Chlorine bleach at a concentration of 10% is the only agent that effectively kills C. diff spores on environmental surfaces. Chlorine bleach at the required concentration is very harsh and produces seriously unpleasant smells and corrosiveness that is potentially dangerous. Also, diluted bleach only provides temporarily disinfection, because once bleach solution is sprayed onto surface and exposed to light and/or air, after a short period of time, almost of all of bleach will be decomposed and loses its disinfecting function.

According to one embodiment, the water soluble N-halamine is preferably one from 1-chloro-4,4,5,5-tetramethyl-imidazolidin-2-one, 1-chloro-2,2,5,5-tetramethylimidazolidin-4-one, 2-chloro-1,3,5-triazine-2,4,6-triamine, N-chloro-4-amino-2,2,6,6-tetramethylpiperidine, 1-chloro-5,5-dimethylhydantoin and 1-bromo-5,5-dimethylhydantoin under neutral or base condition. All of those mono-halogenated N-halamines possess another un-halogenated N—H group; those mono-halogenated N-halamines are weak acids and can be neutralized by most bases, such as sodium hydroxide, potassium hydroxide. Those neutralized N-halamines possess positive charges in aqueous solution. Because of the strong ionic interactions, the neutralized mono-halogenated N-halamines can be bound onto anionic polymer or other negatively-charged polymers with ionic complexes to provide extended shelf-life, improved durability and reduced chlorine odor and toxicity.

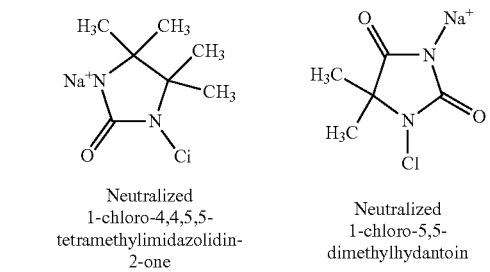

Neutralized 1-chloro-4,4,5,5-tetramethylimidazolidin-2-one

Neutralized 1-chloro-5,5-dimethylhydantoin

According to one embodiment, another prefer water soluble N-halamine is one from the discovered cationic QAMs-based N-halamines including but are not limited to 1-chloro-3-bromoalkyltrimethylammonium-4,4,5,5-tetramethyl imidazolidin-2-one, 1-bromo-3-bromoalkyltrimethylammonium-4,4,5,5-tetramethyl imidazolidin-2-one, 1-chloro-3-bromoalkyltrimethylammonium-2,2,5,5-tetramethyl imidazolidin-4-one, 1-bromo-3-bromoalkyltrimethylammonium-2,2,5,5-tetramethyl imidazolidin-4-one, 2-chloro-4-bromoalkyltrimethylammonium-1,3,5-triazine-2,4,6-triamine, 2-bromo-4-bromoalkyltrimethylammonium-1,3,5-triazine-2,4,6-triamine, 1-chloro-3-bromoalkyltrimethylammonium-5,5-dimethylhydantoin, and 1-bromo-3-bromoalkyltrimethylammonium-5,5-dimethylhydantoin, etc.

According to one embodiment, another preferred water soluble, halogen stabilizing compound is selected from the discovered free radical scavengers including but are not limited to hydroquinone, (2,2,6,6-tetramethylpiperidin-1-yl) oxy, 2,2,6,6-tetramethyl-piperidine-1,4-diol, 2,2,6,6-tetramethyl-4-piperidinol, 4-amino-2,2,6,6-tetramethylpiperidine, 2,2,6,6-tetramethylpiperidine, 2,2,6,6-Tetramethyl-4-piperidyl methacrylate, 2,2,6,6-tetramethyl-4-piperidone, (2,2,6,6-tetramethylpiperidin-4-yl) benzoate, 1,1'-ethylenebis(3,3,5,5-tetramethylpiperazinone), 4-acetamido-2,2,6,6-tetramethylpiperidine, bis(2,2,6,6-tetramethyl-4-piperidyl) succinate, bis(2,2,6,6-tetramethylpiperidin-4-yl) butanedioate, bis(2,2,6,6-tetramethylpiperidin-4-yl)hexane-1,6-diamine and other water soluble derivatives of 2,2,6,6-tetramethyl piperidine.

According to various embodiments, the polymeric binder/binding agent is preferably a water soluble anionic polymer, such as poly(methacrylic acid) (PMAA), poly(acrylic acid)

(PAA), or water soluble polymers that possess negative charges, such as celluloses and their derivatives. In a neutral or basic environment, the PMAA and PAA will be in the form of anionic (—COOH→—COO—), which carries negative charges that form ionic complexes with N-halamines with positive charges. The binding/stabilizing is mainly provided by ionic interactions between the positively-charged N-halamines and negatively-charged polymeric binders. The polymer chains will attract and hold the positively-charged N-halamines in the aqueous solution and their resulting films. This will considerably bind/stabilize the N-halamine molecules into the polymer in the aqueous system and their resulting films, as described above.

The amount of N-halamine in disinfecting fluid is generally sufficient to provide from about 1 to 40% active chlorine and/or bromine. The active chlorine and/or bromine loaded in the solution is typically in an effective amount for deactivating microbes including spores in minutes. Preferably, the active chlorine and/or bromine load of N-halamine maintained in the fluid is from about 1% to 10%.

According to one embodiment of this invention, the disinfecting fluids can be added into commercial wiper and used as disinfecting wiper. According to another embodiment of the invention, the disinfecting fluids can be used as biocidal additives for skin cream and lotion. According to a further embodiment of the invention, the disinfecting and deodorizing fluid can be used as wiping, soaking solution or spray for odor-related substrates including, but not limited to, kitchen areas, shoes, underwear, socks, incontinence pads, garbage bins, garbage bags, garbage tanks, pet beds, cat litter pans, dog pee pads, and animal wastes.

Group 2: Antimicrobial Textiles

According to various embodiments of the invention, it provides a process for the making of an antimicrobial coating for soft surfaces such as fabrics, woven or nonwovens, natural or synthetic or blends thereof. An N-halamine and polymeric binder-containing solution can be applied onto fabrics via spraying or dip-padding or soaking. Once it gets dried, a protective coating of a polymeric binding material containing an effective amount of an N-halamine substance is immobilized onto fabrics to provide potent antimicrobial and odor control functions.

In one embodiment, the textile used may be fabrics regardless of whether spun, knit, or woven, or in nonwoven sheets or webs. In a preferred method, a typical dip-pad-dry process can be used so as to achieve multifunctional textiles of the present invention. An aqueous solution that comprises water soluble/dispersible N-halamine, a water soluble/dispersible polymeric binder and a wetting agent can be added in the finishing bath. Examples of suitable wetting agents include, but are not limited to, sodium dodecyl sulfate, Triton X-100, Nonoxynol-9, Polysorbate, Glyceryl laurate. Otherwise wetting agents suitable for use in the present invention will be known to and used by those of skill in art.

Those of skill in the art will readily appreciate that the concentration of various components of the aqueous finishing bath can be widely varied depending upon the particular components employed and the resulting performance desired. Typically, the N-halamine is present at a concentration ranging from about 0.1% to 20% active halogen, more preferably at a concentration ranging from about 0.5% to 10% active halogen. The concentration of polymeric binder employed will depend on the concentration of the N-halamine employed. Typically, the ratio of N-halamine to polymeric binder present will range from about 10:1 to 1:10. The pH of the aqueous bath will typically range from about 3 to 10 and, more preferably, from a pH of about 4 to 8. The wetting agent is typically present at a concentration which is within the range of about 0.01% to about 1%.

According to various embodiments of the invention, it provides a process for the making of a multifunctional coating for non-woven fabrics; the resulting non-woven can be used as uniforms, surgical gowns, drapes and linens, etc. in hospitals to inactivate the pathogens. For non-woven coating techniques, 0.1 to 20% N-halamine can be employed via a simple embodiment of durable process (DP) finishing. Various embodiments of the invention, by providing a plurality of multifunctional non-woven fibers into a collection, include but are not limited to masks or air filters. A suitable method of inactivating pathogenic microorganisms and viruses, or oxidize-able noxious vapors contained in air streams by contacting the air stream with the mask or filter is provided.

Group 3: Multifunctional Coating

According to various embodiments of the invention, it provides a process for the making of a multifunctional coating for hard surface like as metal, wood, plastic, paint, etc. An N-halamine and polymeric binder solution can be applied onto targeted surfaces via spraying or wiping. Once the surfaces get dried, a protective clear film of a polymeric binding material containing an effective amount of a N-halamine substance is immobilized onto the hard surface.

Currently, 10% chlorine bleach is the only agent that effectively kills C. diff spores on environmental surfaces. However, chlorine bleaching disinfecting spray cannot provide a persistent germicidal function for the targeted surfaces. Once bleach solution is sprayed onto surface and exposed to light and/or air, bleach will be decomposed and loses its biocidal function after a short period of time, usually in minutes. C. diff spores can live up to 5 months on environmental surfaces. A disinfecting spray which provides persistent self-decontamination for targeted surfaces will provide promising benefits in the healthcare setting to prevent hospital associated infections.

According to various embodiments, the present disclosure provides a composition and method that is capable of forming an antimicrobial and deodorizing coating on at least one surface on targeted objects. Specifically, use of anionic or negatively-charged polymeric binder as film-forming materials to immobilize cationic N-halamines onto targeted surfaces to increase the durability of available biocidal N-halamines and control the functions and persistence in various applications.

In specific embodiments, the water soluble N-halamine is preferably at least one cationic N-halamine from the following Quaternary Ammonium Moieties (QAMs)-based N-halamines including, but not limited to, 1-chloro-3-bromoalkyltrimethylammonium-4,4,5,5-tetramethyl imidazolidin-2-one, 1-bromo-3-bromoalkyltrimethylammonium-4,4,5,5-tetramethyl imidazolidin-2-one, 1-chloro-3-bromoalkyltrimethylammonium-2,2,5,5-tetramethyl imidazolidin-4-one, 1-bromo-3-bromoalkyltrimethylammonium-2,2,5,5-tetramethyl imidazolidin-4-one, 2-chloro-4-bromoalkyltrimethylammonium-1,3,5-triazine-2,4,6-triamine, 2-bromo-4-bromoalkyltrimethylammonium-1,3,5-triazine-2,4,6-triamine, 1-chloro-3-bromoalkyltrimethylammonium-5,5-dimethylhydantoin, and 1-bromo-3-bromoalkyltrimethylammonium-5,5-dimethylhydantoin, etc. The alkyl can be lower alkyl of 4 to 12 carbons.

In specific embodiments, the polymeric binder/stabilizing agent is preferably at least one from water soluble or water dispersible negatively-charged polymers. Those polymers carry negative charges and can form ionic complexes with positively-charged N-halamines. The negatively-charged polymer chains will attract and hold the positively-charged N-halamines in the aqueous solution and their resulting films, and ionic interactions will provide strong binding/stabilizing capability.

In specific embodiments, the preferred water soluble halogen stabilizing compounds is one from the discovered free radical scavengers including but not limited to (2,2,6,6-tetramethylpiperidin-1-yl)oxy, 2,2,6,6-tetramethyl-piperidine-1,4-diol, 2,2,6,6-tetramethyl-4-piperidinol, 4-amino-2,2,6,6-tetramethylpiperidine, 2,2,6,6-tetramethylpiperidine, 2,2,6,6-Tetramethyl-4-piperidyl methacrylate, 2,2,6,6-tetramethyl-4-piperidone, (2,2,6,6-tetramethylpiperidin-4-yl) benzoate, 1,1'-ethylenebis(3,3,5,5-tetramethylpiperazinone), 4-acetamido-2,2,6,6-tetramethylpiperidine.

The amount of N-halamine immobilized into coating is generally sufficient to provide from about 5 to 40% active halogens. The N-halamines loaded into coatings are typically an effective amount for deactivating microbes, degrading malodorous or noxious compounds or inactivating enzymes that are responsible for catalyzing reactions that generate malodorous compounds from organic substrates. Preferably, the active halogen maintained on the medium is from about 10% to 20%. The amount of polymeric binder is generally sufficient to provide from about 20 to 50% of the formed coating. Preferably, the polymer content maintained in the coating is from about 30% to 40%.

Group 4: Antimicrobial and Deodorizing Medium

According to various embodiments, the present invention provides a composition and method to provide disposable antimicrobial and deodorizing media. The potential applications for such antimicrobial and deodorizing media include but are not limited to biohazard absorbent, antimicrobial cat litter, odor control cat litter, refrigerator deodorizer and other odor-related products. The potential media include but are not limited to sand, zeolite, glass beads, clay, corncobs, grass, wood, and plastic fibers.

N-halamines have been employed in oxidative decontamination of odor-generating microorganisms. N-halamines also can destroy the chemical compounds causing odor through oxidative reactions. The present invention provides a composition and method to produce a stable N-halamine coated medium. The treated medium can be used for inactivating microorganisms and neutralizing odor chemicals in a wide range of applications, such as for the inactivation of biological fluids, and reduction or elimination of microorganisms and neutralization of odor from animal waste, etc. Such coatings may also deactivate noxious compounds such as toxins in pesticides or agents of chemical warfare.

Free chlorine or bromine is able to effectively degrade chemicals by oxidative reactions. N-halamine structures are capable of converting sulfides, such as hydrogen sulfide, carbon disulfide, dimethyl disulfide and other alkyl disulfides to sulfoxides and sulfones, mercaptans to hydrocarbon disulfides and then to sulfoxides and sulfones, alcohols/aldehydes to ketones and then to carboxylic acids under extreme oxidizing conditions, and cyanides to carbon dioxide and ammonium in water. The resulting carboxylic acids can be captured by the remaining amide, imide or amine groups from N-halamines. The extreme oxidative power of N-halamines will destroy most of the targeted chemical compounds and create hazard-free, non-odorous end products.

Specifically, litter box odor can be the toughest part of living with a cat. Using odor control cat litter in the litter box can go a long way to creating and maintaining a fresher smelling house. The amount of immobilized N-halamine on the litter substrate is generally sufficient to provide about 0.01 to 2% active halogen. The active halogen loaded on the medium is typically an effective amount for deactivating microbes and preventing and degrading odor, including by inactivating enzymes responsible for malodorous end products of microbial metabolism. Preferably, the active halogen content maintained on the medium is from about 0.1% to 1%.

The present invention features a clumping animal litter composition comprising: zeolite, a surface-active substance and a clumping agent. The zeolite is coated with the surface-active substance, and then with the clumping agent. In one embodiment, the clumping animal litter composition is a clumping cat litter composition.

In one embodiment of this invention, the inorganic medium is naturally-occurring. The naturally-occurring inorganic medium can be sand, zeolites, clay, porcelain, bentonite, chalk, limestone, sand, diatomite, and sepiolite. In one embodiment, the zeolite may also be a combination which includes one or more zeolites. In one embodiment, the zeolite is Clinoptilolite. The zeolite can have a purity of between about 50% and about 98%. In one embodiment, the zeolite has a purity of between about 94% and about 99%. In any case, these inorganic particulate materials can be employed in making the animal litter compositions of this invention and an array of additional products.

The surface-active substance (surfactant) can be sodium sulfate, potassium sulfate, sodium phosphate, sodium pyrophosphate, sodium carbonate, potassium stearate, aluminum potassium sulfate or aluminum sulfate, or a combination of one or more of these compounds. In one embodiment of this invention, the surface-active substance is sodium sulfate or potassium sulfate. In another embodiment of this invention, when the zeolite has a moisture content of greater than 5%, the sodium sulfate is anhydrous sodium sulfate.

The clumping agent can be sodium bentonite, cellulose, guar gum, chitosan, *psyllium*, agar, algin, starch, carrageenan, gum arabic, gum ghatti, gum tragacanth, karaya gum, larch gum, locust bean gum, pectin, quince seed gum, tamarind gum or xanthan gum or a combination of one or more of these compounds.

It is well known that bentonite can be used to cause swelling of clay. In a hydrated state, sodium bentonite often exhibits a tackiness which will cause adjacent particles of the swelling clay to agglomerate. The tackiness of the swelling clay gives it a "glue-like" function in the clumping process. The cohesiveness of the clump is tied to the particle distribution of swelling clay within the clay blend that forms the clump; removal of animal urine wastes from soiled litter is facilitated by the formation of clumps.

In one embodiment of this invention, the clumping agent is sodium bentonite, the cellulose has a purity of about 90% to about 99% and/or a mesh size of 200-325. In another embodiment of this invention, the clumping agent is cellulose. In other embodiments, the cellulose has a purity of about 90% to about 99% and/or a mesh size of 60-200. The clumping agent will typically be present in the animal litter composition containing sodium bentonite at a level which is within the range of 20 to 40 weight percent and will preferably be present at a level within the range of 30 to 35 weight percent. In such animal letter compositions the sodium bentonite will typically be present at a level of at least 55 weight percent and will more typically be present at a level of at least 60 weight percent, at least 65 weight percent, or even more than 70 weight percent.

Animal litter can be manufactured in accordance with this invention by utilizing treated deodorizing media consisting of an inorganic particulate material, such as zeolite, perlite, or clay which is coated with a N-halamine at a level of 0.1% to 10% and a binder at a level of 0.05% to 1.0%. The particulate matter will typically be coated with 0.2 to 5 weight percent of a N-halamine and 0.1 to 0.2 weight percent of the binder. The inorganic particulate material will typically be present in the animal litter at a level of at least 70 weight percent and will more typically be present at a level of at least 80 weight percent. In accordance with this technique the N-halamine solution is applied to the particulates by spraying or mixing in a vessel. Other additives such as surfactants or binders can be used to enhance the mixing and binding to the substrate. The particulates are typically then dried to 10% or less moisture in a commercial drying apparatus to insure free flowing particulates. Driers may be of any convenient low intensity types including, but not limited to, tray driers, fluidized bed driers, jet driers, tumble driers, rotary vacuum driers and ribbon blenders. Drying in forced air or ambient conditions is also possible.

In a specific procedure a zeolites base clumping animal litter of the present invention was also manufactured according to the following procedure. Clinoptilolite zeolite (St. Cloud Zeolite, Winston, New Mexico) (at least 97% pure, having a 14-40 mesh) was used as the starting material. Anhydrous sodium sulfate (2% by weight), in dry form, was then applied to the zeolite while mixing the reagent by agitation to ensure proper surface coating of the zeolite. The compound was then mixed again and commercially available hydroxyethyl cellulose (2%; mesh size 20-80), MCDMH (0.25%, mesh 100-200), sterically hindered amine (0.025%) and TMIO (0.025%). Clumping testing has demonstrated the zeolite clumping litter has superior properties as a clumping litter. The odor control of the zeolite-containing litter was noticeably improved over the commercial available bentonite-containing litter.

In summary, compared with the current technologies, this invention provides simple, practical, flexible, user-friendly and cost-effective approaches to provide soft and hard surfaces with stable, potent antimicrobial and deodorizing functions through the formation of coatings that persistently express halogen-based oxidizing power. The multifunctional coatings can directly degrade malodorous and noxious compounds, and therefore bring about odor control not only by direct effects on microbes that are responsible for generating malodors, but by degrading the end products of microbial production, and inhibiting microbial enzymes released into the environment to catalyze reactions that generate malodorous end products.

Example 1

This example illustrates the comparison of different disinfecting fluid formulae. Three aqueous N-halamine solutions were made, one with no other components in addition to the N-halamine, one with the addition of a binding agent/stabilizing constituent, and one with the addition of a halogen stabilizer. For the control, Sample 1, 10 grams of 2-chloro-1,3,5-triazine-2,4,6-triamine and 0.05 gram of Triton X-100 were added into 1000 ml of deionized water. For Sample 2, 10 grams of 2-chloro-1,3,5-triazine-2,4,6-triamine, 3 grams of guar gum, and 0.05 gram of Triton X-100 were added into 1000 ml of deionized water. For Sample 3, 10 grams of 2-chloro-1,3,5-triazine-2,4,6-triamine, 0.5 gram of 2,2,6,6-tetramethyl-4-piperidyl methacrylate, 3 grams of guar gum, and 0.05 gram of Triton X-100 were added into 1000 ml of deionized water. After 24 hours of agitation under room temperature, a clear solution was achieved for sample 1; a clear and slightly thick solution was achieved for Samples 2 and 3. Laboratory personnel identified Sample 1 as having an objectionable chlorine smell, whereas Sample 2 had only a mild chlorine smell. Sample 3 had a mild fresh smell, not obviously attributable to chlorine. The results suggest that an effective way to reduce chlorine odor and gas phase corrosion risk due to volatilized chlorine is to add binding agent/stabilizing agent or free radical scavenger to the aqueous fluid containing N-halamine.

Example 2

This example illustrates the capacity of the aqueous N-halamine fluids to be taken up by a fabric substrate using a typical dip-pad-dry procedure commonly applied in finishing textile fabrics. A finishing bath containing 20 grams of 1-chloro-5,5-dimethylhydantoin, 2 grams of 2,2,6,6-Tetramethyl-4-piperidyl methacrylate, 3 grams of hydroxyethyl cellulose, and 0.2 gram of Triton X-100 in 1000 ml of deionized water was prepared. Then for the "dip-pad-dry" procedure, 200 grams of polypropylene non-woven fabric were dipped in the bath at room temperature for at least 5 min to absorb components from the aqueous finishing bath. The fabrics were put into a laboratory wringer to remove the excess solution, resulting in more than 60% wet pickup of the fluid finish. The fabric was dried at a temperature of 80° C. and used to demonstrate functions acquired by the textile attributable to the finish.

Example 3

Textile samples prepared with a finish as described in Example 2 were tested to measure the active chlorine contents by iodometric titration as an indicator of the successful application of a finish coating to the synthetic fibers of the textile. 0.5-1 g of coated fabrics were cut into fine fragments, and treated with a solution of one g of KI in 100 mL of deionized water (the solution contained 0.05% (v/v) of TX-100) at room temperature under constant stirring for 1 hour. The amount of Iodine ($I_2$) formed was titrated with standardized sodium thiosulfate aqueous solution. The uncoated fabrics were tested under the same conditions to serve as controls. The available active chlorine content on the fabrics was calculated according to equation (1):

$$Cl\% = \frac{35.5}{2} \times \frac{(V_S - V_0) \times C_{Na_2S_2O_3}}{W_S} \times 100 \qquad (1)$$

where $V_S$, $V_0$, $C_{Na2S2O3}$ and $W_S$ were the volumes (mL) of sodium thiosulfate solutions consumed in the titration of the coated and uncoated samples, the concentration (mol/L) of the standardized sodium thiosulfate solution, and the weight of the chlorinated sample (mg), respectively. By adjusting the coating fluid concentration used in textile treatment, a series of polypropylene fabrics was obtained with active chlorine contents of 558, 1080, 2952 and 4960 ppm, respectively, demonstrating the acquisition of sufficient chlorine to confer functionality on the fabrics created through a finishing method common to the industry.

Example 4

The finished fabric samples tested for chlorine content in Example 3 were tested for antibacterial properties of the chlorine contents that were measured on each one. Antibacterial tests were conducted according to a modification of AATCC Test Method 100-1999. All tests were performed in a Biosafety Level 2 hood. In this study, Staphylococcus aureus (S. aureus, ATCC 6538) and Escherichia coli (E. coli, ATCC 15597) were used as typical examples of Gram-positive and Gram-negative bacteria, respectively. Candida albicans (C. albicans 10231) was employed to challenge the antifungal activities of the samples, and E. coli bacteriophage MS2 15597-B1 virus was used to represent viral species. Bacillus subtilis spores obtained from North American Science Associates (Northwood, Ohio; Lot No. N24609) were used to challenge the sporicidal properties of the treated fabrics.

The coated fabrics with demonstrable chlorine contents showed potent biocidal efficacy against a wide range of microorganisms. Shown in Table 1 are typical results for Gram-negative bacteria, Gram-positive bacteria, fungi, viruses and spore. Higher active chlorine contents in the finished textile samples led to more potent biocidal efficacies. At 4960 ppm chlorine content, the treated fabrics provided a total kill of $10^8$-$10^9$ CFU/mL for S. aureus, E. coli, and C. albicans in only 3 minutes or less. MS2 virus appeared to be more resistant than the bacterial and fungal species tested: at the same chlorine content, it took 10 minutes for the fabrics to offer a total kill of $10^6$-$10^7$ PFU/mL for the virus. These exceptional biocidal activities point to great potential for the treated fabrics for a wide range of infection control applications, particularly for those where fast and broad-spectrum efficacies are required. Bacterial spores are much more difficult to kill than vegetative forms of bacteria and fungi, and of viral particles. The treated fabrics provided a total kill of test challenge spores after an exposure of 10 minutes. These results further support the potential of the treated fabrics for healthcare industry applications.

TABLE 1

Antibacterial activities of treated fabrics with various active chlorine contents resulting from an aqueous finishing bath exposure

| Active chlorine content | Minimum contact time for a total kill (min) | | | | |
|---|---|---|---|---|---|
| (ppm) | S. aureus | E. coli | C. albicans | MS2 virus | Spore |
| 558 | 30 | 30 | 60 | 120 | N/A |
| 1080 | 15 | 15 | 30 | 60 | 480 |
| 2952 | 2 | 2 | 5 | 15 | 120 |
| 4960 | 1 | 1 | 3 | 10 | 10 |

Example 5

The purpose of these tests was to determine the efficacy and surface persistence of two different water-based disinfecting fluid formulations when applied to hard surfaces as a spray. Formica swatch samples from Home Depot were used as the test pieces. Formica samples included both smooth and textured surfaces. Two formulations both containing 1% N-halamine were used as disinfecting fluid. Formica test samples (coupons) were sprayed, air dried at room temperature, and stored for 15 minutes, 24 hours, 7 days and 2 months under normal laboratory conditions in the dark. The antimicrobial testing was performed according to a modified Japanese Standards Association protocol, ISO 22196:2007/JIS Z 2801:2000 titled "Antimicrobial products-Test for antimicrobial activity and efficacy."

Procedure

Each test piece was cut into squares with 50 mm±2 mm each side. The test pieces were sterilized with dry heat to minimize warping by wrapping test pieces in aluminum foil and placing them in an oven at 180° C. for 30 minutes. Test pieces were then sprayed with the 1% disinfecting spray and allowed to air dry. Test pieces were sprayed and stored up to 2 months prior to testing. Unsprayed samples served as controls.

Test Inoculum Preparation

One day prior to testing, an S. aureus overnight culture was prepared by using a sterile 4 mm inoculating loop to transfer one loop-full of bacteria from a TSA plate onto a Nutrient Agar (NA) slant. After overnight culture at 34-36° C., a loop-full of bacteria was transferred into 10 mL of 1:500 nutrient broth by dragging a sterile 4 mm inoculating loop in a straight line up the length of the slant. If it was necessary, 1:500 Nutrient Broth (NB) was used to arrive at a final challenge concentration of $6 \times 10^5$ cfu/100 µL.

Antimicrobial Testing Procedure

Parafilm film was cut into squares with 40 mm±2 mm each side. Prior to testing, each piece of parafilm was cleaned with ethanol and allowed to air-dry. Aseptically the carrier test pieces were transferred into sterile petri-plates. Each test piece was inoculated with 100 µL of the challenge inoculum. Test pieces were covered with a piece of clean parafilm and gently pressed so that the challenge inoculum spread over the parafilm area making sure that inoculum did not spill over the edge of the parafilm. Petri-plates were allowed to sit in the bio-safety cabinet at room temperature for 30 minutes. After the 30 minute contact time had elapsed, sterile tweezers were used to carefully transfer each of the treated and untreated test pieces into individual sterile Whirl-Paks containing 10 mL of SCDLP broth.

Test pieces were massaged in neutralizing solution for at least thirty seconds. 10-fold serial dilutions of the SCDLP broth in DPBS were prepared. The SCDLP broth and dilutions were placed onto Plate Count Agar (PCA) using the spread-plate method, and plates were incubated at 34-36° C. for 48 hours. After the incubation period, the plates were used to establish colony plate counts so as to calculate the corresponding Log Reduction values (LRV).

Results

As shown in Table 2, when treated with 1% disinfecting spray formulations, the coated hard Formica surfaces showed persistence of high levels of antimicrobial efficacy even after two months. After two months, the surfaces, both smooth and textured provided more than 3 LRV of challenge test organisms. The results demonstrate the high level of antimicrobial activity of surfaces treated with aqueous formulations of N-halamine, and the persistence of those levels of efficacy over at least two months post treatment.

TABLE 2

Antimicrobial efficacy and persistence on hard surfaces coated with water-based N-halamine formulations, and challenged with S. aureus

| Sample Description Disinfecting fluid | Post | Dry | Substrate | CFU/100 µL | LRV |
|---|---|---|---|---|---|
| #1 | 15 min | air dried | Textured, black | 2.00E+00 | 7.17 |
| #1 | 15 min | Wiped | Smooth, white | 1.00E+00 | 7.48 |
| #2 | 15 min | Air-dry | Textured, black | 1.00E+00 | 7.48 |
| #2 | 15 min | Air-dry | Smooth, white | 8.40E+01 | 5.55 |
| #2 | 15 min | Wiped | Textured, black | 0.00E+00 | 7.48 |

TABLE 2-continued

Antimicrobial efficacy and persistence on hard
surfaces coated with water-based N-halamine formulations,
and challenged with S. aureus

| Sample Description Disinfecting fluid | Post | Dry | Substrate | CFU/100 µL | LRV |
|---|---|---|---|---|---|
| #1 | 24 h | Air-dry | Textured, black | 1.50E+01 | 6.3 |
| #1 | 24 h | Air-dry | Smooth, white | 1.00E+00 | 7.48 |
| #2 | 24 h | Air-dry | Textured, black | 4.00E+00 | 6.88 |
| #2 | 24 h | Air-dry | Smooth, white | 5.00E+00 | 6.78 |
| #1 | 7 d | Air-dry | Smooth, white | 1.35E+02 | 5.55 |
| #2 | 2 m | Air-dry | Smooth, tan | 1.20E+04 | 3.34 |
| #2 | 2 m | Wiped | Textured, tan | 6.00E+00 | 6.64 |
| Unsprayed Control | | Air-dry | Textured, black | 3.40E+08 | — |
| Unsprayed Control | | Air-dry | Smooth, tan | 3.50E+08 | — |
| Sterility Control | | | Textured, black | 0.00E+00 | — |

Example 6

The Effect of Binding Agent on Durability of Antimicrobial Hard Surface

The purpose of this testing as to determine the contribution of binding agent in the water-based N-halamine formulation on durability of antimicrobial function on hard surfaces. Formica coupon samples with textured surfaces were used as the test articles. Two formulations containing 1% N-halamine with or without binding agent were used as disinfecting fluids applied to the coupons. Formulation #1 contained 0.2% hydroxethyl cellulose; Formulation #2 did not contain any binding agent. Formica test coupons were sprayed and then stored in a Germfree BZ 3SSRX biosafety hood with laminar air flow. The laminar flow exposure of the coupons was used to simulate accelerated aging conditions. After 72 hours of exposure, antimicrobial testing was performed with 30 minutes of contact.

Results

As shown in Table 3, the Formica coupons treated with the aqueous formulation containing binding agent provided superior antimicrobial durability, to the extent of several orders of magnitude when assessed by LRV.

TABLE 3

Antimicrobial efficacy of coated hard surfaces against S. aureus

| Description Disinfecting fluid | Sample | LRV |
|---|---|---|
| formula one with hydroxyl cellulose | #1 | 5.32 |
| | #2 | 6.43 |
| | #3 | 4.51 |
| formula two without hydroxyl cellulose | #1 | 3.76 |
| | #2 | 3.32 |
| | #3 | 1.43 |

Example 7

The purpose of this experiment was to measure the influence of binder on chlorine release from surfaces exposed to formulations of the water-based fluids containing N-halamine. The substrate in these experiments was particulate zeolite coated with the test formulation, air dried and stored at ambient temperature. In this test, 20 kg of clinoptilolite zeolite particles (14-40 mesh) were mixed with 0.05 kg of MCDMH (Lonza Inc) in 2 liters of water in a cement mixer rotating at 10 revs/min for 10 minutes, and allowed to air dry at 25° C. for 2 weeks with daily manual agitation until the moisture content was 9% (Sample 1). In another batch, 20 kilos of zeolite particles of the same size range were mixed with 0.05 kg of MCDMH plus 0.008 kg of hydroxyethylcellulose binder in 2 L of water in a cement mixer rotating at 10 rev/min. At the end of this period the material was air dried in an oven to 9% moisture (Sample 2). Both sets of zeolite particles showed similar quantities of bound chlorine upon testing colorimetrically with KI.

The extent of the chlorine odor associated with the dried zeolites was determined. One hundred g of the dried zeolites was stored in a 1.25 liter sealed glass container.

After 1 week of storage, chlorine odor in the headspace above 100 grams of zeolites was measured. Each test was repeated 3 times. Sample 1 and Sample 2 indicated 100 ppm and 90 ppm in headspace, respectively, indicating that the presence of the binder reduced the extent of chlorine emanation from the coating on the solid porous particles.

Example 8

The purpose of this experiment was to determine the influence of sterically hindered amine (SHA) on release of chlorine from solid particles coated with an aqueous N-halamine (MCDMH) and stored. The procedure used preparations of zeolite that were made by the admixture of MCDMH and particles in the presence or absence of 0.005 kg of SHA, in the proportions described in Example 1. Once again the 100 gram sample of dried coated zeolite was stored in sealed a glass container for one week. The chlorine level in the headspace above this sample was then measured. Each test was repeated 3 times. Sample 3 indicated 50 ppm of chlorine in headspace, compared to 100 ppm in Sample 1. The results show the beneficial effect of the halogen stabilizer in the formulation in reducing the emanation of chlorine from the treated particles.

Example 9

The purpose of this experiment was to measure the effect of binder plus SHA on retention of chlorine in air dried coatings of water-based N-halamine formulations on a hard surface substrate. The procedure used one gram of MCDMH with or without 0.2 grams of hydroxyethylcellulose binder and 0.1 grams of SHA dissolved in 100 ml of water as the surface treatments. Solutions of MCDMH, MCDMH plus binder and SHA containing equivalent amounts of oxidative chlorine were applied to 9 $cm^2$ of hard surface substrate (Formica coupons), and allowed to dry at room temperature in a chemical fume hood. Determinations of chlorine levels per $cm^2$ were made on coupons sampled after 4 hours, 24 hours, 48 hours, and 96 hours. The chlorine remaining on each surface was measured by iodometric titration of solutions obtained after soaking of test samples in deionized water for 1 hour at room temperature. The results are reported in Table 4.

TABLE 4

Effect of binder plus SHA on retention of Cl in
air dried coatings on hard surface substrate

| | Chlorine Content ($\times 10^{18}$ Cl/cm$^2$) Time | | | |
|---|---|---|---|---|
| | 4 h | 24 h | 48 h | 96 h |
| MCDMH | 3.61 | 3.25 | 3.01 | 2.75 |
| MCDMH plus binder/SHA | 6.22 | 6.20 | 6.17 | 6.05 |

The results show that there was a much higher retention of active chlorine on surfaces treated with the N-halamine formulation containing the binder/SHA combination, indicating much lower levels of chlorine loss on storage. The superior retention was several orders of magnitude greater than in the formulation without these additional components.

Example 10

The purpose of this experiment was to measure the beneficial effect of binder plus SHA on retention of chlorine in air dried coatings of N-halamine formulations on a soft surface substrate. Solutions of MCDMH, MCDMH plus hydroxyethylcellulose binder plus SHA, each containing equivalent amounts of oxidative Cl were applied to 9 cm$^2$ of soft surface substrate (cotton fabrics or paper), and allowed to air dry at room temperature in a chemical fume hood. Determinations of chlorine per cm$^2$ were made on fabrics sampled after 4 hours, 24 hours, 48 hours, and 96 hours. The remaining chlorine was measured by iodometric titration after soaking of test samples in deionized water for 1 hour at room temperature. The results are shown in Table 5.

TABLE 5

Effect of binder plus SHA on retention of Cl in air dried
N-halamine coating formulations on soft surface substrates

| Materials | | Chlorine Content ($\times 10^{18}$ Cl/cm$^2$) Time | | | |
|---|---|---|---|---|---|
| | | 4 h | 24 h | 48 h | 96 h |
| Cotton | MCDMH | 2.41 | 2.04 | 1.56 | 0.89 |
| | MCDMH plus binder/SHA | 5.55 | 5.38 | 4.97 | 4.81 |
| Paper | MCDMH | 2.74 | 2.12 | 1.87 | 1.04 |
| | MCDMH plus binder/SHA | 4.35 | 4.15 | 4.01 | 3.76 |

The results show the beneficial effects of the formulation additives on the retention of bound chlorine on treated soft surfaces. The improvement was again measured as several orders of magnitude better in Cl/cm sq.

Example 11

The purpose of this experiment was to show the effect of binder plus SHA on retention of chlorine in air dried coatings on a porous substrate. Solutions of MCDMH, MCDMH plus hydroxyethylcellulose binder and SHA containing equivalent amounts of oxidative chlorine were applied to 50 grams of porous substrate (clinoptilolite Zeolites), and all samples were allowed to dry at room temperature in a chemical fume hood. The procedure used 5 grams of treated zeolites with or w/o binder/SHA placed in a 20 ml column, and 100 ml of water was allowed to flow by gravity through each column. The concentration of the chlorine in the output fluid and the concentration of chlorine that remained in the coated zeolites were measured. The results of this experiment are shown in Table 6.

TABLE 6

Effect of binder plus SHA on retention of Cl
in air dried coatings on porous substrate.

| | Chlorine Content | | | |
|---|---|---|---|---|
| | Output | | Remained on substrate | |
| Coated Zeolites | ppm | % | ppm | % |
| MCDMH | 479 | 88.8 | 60 | 11.2 |
| MCDMH plus binder/SHA | 318 | 61.3 | 201 | 38.7 |

The results show that much more chlorine left the zeolite treated with aqueous N-halamine alone, without binding agent and stabilizer, and correspondingly less chlorine was retained and measurable on the surface of these particles.

Example 12

The present invention relates to the use of wide range of N-Halamine compounds as urease inhibitors whereby the inhibition of the enzymes is a contributing mechanism to odor control resulting from the aqueous formulations. Ureases belong to the superfamily of amidohydrolases and phosphotriesterases. These catalyze the hydrolysis of urea into carbon dioxide and ammonia. The reaction occurs as follows:

$$(NH_2)_2CO + H_2O \rightarrow CO_2 + 2NH_3$$

When urease catalyzes the hydrolysis of urea to produce ammonia and carbamate, the carbamate produced is subsequently degraded by spontaneous hydrolysis to produce another ammonia and carbonic acid. Urease activity tends to increase the pH of its environment as it produces ammonia. Ureases are nickel-containing metalloenzymes of high molecular weight, and depend on S containing amino acids for their conformational integrity and hence their enzymatic functionality. Many other enzymes that contribute to malodor generation from organic substrates have similar contents of S-containing amino acid residues and are dependent upon them for conformational integrity and in some cases, the structure of the active catalytic sites.

Test Methods

Urease inhibitor activity can be evaluated in aqueous systems. Urea plus a test compound with possible urease inhibition activity and relatively pure urease enzyme are incubated together to determine the effect on urease-catalyzed hydrolysis of urea. We used this test to show the inhibitory effect of an N-halamine formulation. The tests were conducted at 25° C. using purified Jack Bean urease enzyme, (50,000-80,000 units per g): a unit of urease will liberate 1 mole of NH$_3$ from urea per minute at pH 7.0 at 25° C.

1 ml 1 wt % N-halamine as enzyme inhibitor was added into 10 mL 0.001 wt % Jack Bean urease enzyme solutions, and this was allowed to sit at 25° C. for 3 minutes. This combined solution was transferred into a 1.25 L glass vessel with 20 ml 0.1% urea solution; each vessel was sealed with plastic film, allowed to sit undisturbed at 25° C. for 24 hours.

Ammonia content in the headspace of each carrier vessel was then determined using an ammonia test meter.

Tests without inhibitor were performed under the same conditions to serve as control. 10 mL 0.001 wt % Jack Bean urease enzyme solution was transferred into a 1.25 L glass vessel with 20 ml 0.1% urea solution; each vessel was sealed with plastic film, and allowed to sit undisturbed at 25° C. for 24 hours. Ammonia content in the headspace of each carrier vessel was determined using an ammonia test meter. Each test was repeated three times, and the average was recorded. Results:

In the presence of N-halamine the urease was inactivated so that no ammonia product became detectable under the test conditions. The observation was also made that the addition of N-halamine solution to urease solution caused a hazy precipitation to form, indicating likely insolubilization of denatured proteinaceous enzyme.

TABLE 7

| Head space ammonia content | | |
|---|---|---|
| Ammonia Content | Control | Sample |
| ppm | 78 | 0 |

The results indicate that the N-halamine in aqueous formulations made as in Example 1 has intrinsic inhibitory activity sufficient to contribute to effective odor control. This high level of proteinaceous enzyme inhibition is likely to affect other enzymes with dependence on amino acid residues that are susceptible to chlorine mediated oxidation.

Example 13

The purpose of this experiment was to demonstrate that a synthetic porous solid particulate (calcium silicate granules in the form of Catsan® cat litter purchased at retail in the UK) was also suitable for coating with the aqueous deodorizing formulations described in Example 1. N-halamine aqueous fluid formulation was made by mixing 0.025 kg of MCDMH (Lonza Inc.), 0.005 kg of hydroxyethylcellulose, and 0.0025 kg sterically hindered amine in 1 liter of water. 5 kg of synthetic calcium silicate granules were mixed with 1 liter of N-halamine solution in a cement mixer rotating at 10 revs/min for 10 minutes, and allowed to air dry at 25° C. for 2 weeks with daily manual agitation until the moisture content was 8%. The chlorine content was measured by iodometric titration after soaking of test samples in deionized water for 1 hour at room temperature. The treated synthetic calcium silicate granular substrate contained 336 ppm active chlorine, comparable to the previous experiences with a natural porous substrate (Zeolite). Chlorine concentrations of this order are associated with high levels of odor control when used as potential cat litter media. The results illustrate the scope of susceptible solid inorganic particulates that can be successfully coated with the N-halamine formulations described in Example 1.

Example 14

The purpose of this experiment was to demonstrate that the deodorizing coating formulations containing N-halamines described in Example 1 could also be successfully applied to organic particulate substrates. Saw dust in the form of Feline Pine™ Original cat litter was purchased at retail in the United States. N-halamine aqueous coating solution was made from mixing 10 g of MCDMH (Lonza Inc), 2 g of hydroxyethylcellulose, and one g sterically hindered amine in 1 liter of water. 2 kg Feline Pine Original particles with the appearance of saw dust were mixed with 1 liter of N-halamine solution in a cement mixer rotating at 10 revs/min for 10 minutes, and allowed to air dry at 25° C. for 2 weeks with daily manual agitation until the moisture content was 8%. The chlorine content was measured by iodometric titration after soaking of test samples in deionized water for 1 hour at room temperature. The treated saw dust contained 465 ppm active chlorine. Chlorine concentrations of this order are associated with high levels of odor control in tests of materials used as cat litter. The results illustrate the scope of substrates that can be successfully coated with the aqueous formulations of N-halamine described in Example 1.

Example 15

These experiments were performed to demonstrate that the utility of the N-halamine deodorizing formulations in preparing odor control animal litter media is fully consistent with the introduction of clumping functionality to meet commercially desirable needs. The clumping component chosen for these experiments was bentonite clay.

The clumping animal litter of the present invention was manufactured as follows. Clinoptilolite zeolite (KMI Zeolite, Inc., Sandy Valley, Nev.) at least 96% pure, and having a size range of 12-30 mesh was used as the starting material. MCDMH, HEC and SHA were added into water at a concentration of 2.5%, 0.3% and 0.25%, respectively. The aqueous fluid was then applied to the zeolite to reach 15 wt % wet pickup while agitating the mixture to ensure proper surface coating of the zeolite. The coated zeolite was then agitated for 10 min to ensure water dispersion consistency in the compound. Commercially available sodium bentonite (30% by weight, mesh size 200+) was then added to the compound while it continued to mix. The product was then transferred onto a flat concrete floor and allowed to air dry at 25° C. for 2 weeks with daily manual agitation until the moisture content was 8%. The chlorine content was measured by iodometric titration after soaking of test samples in deionized water for 1 hour at room temperature. The chlorine content of the litter (548 ppm) was consistent with the levels needed for high level odor control in soiled litter, and on addition of water to simulate a deposit of animal urine, there was rapid and effective clump formation. The results illustrate the compatibility of the deodorizing formulations used to coat zeolite litter particles with the addition of clumping additives so as to achieve a commercially attractive outcome.

Example 16

In these experiments the efficacy of the disinfecting and deodorizing formulations described in Example 1 and applied as an odor control coating on zeolite particulate cat litter medium, was compared with those of commercially available litter products all of which claim odor control benefits. Commercially available litters were purchased at retail in the United States (Purina's Tidy Cat® clumping litter, Church & Dwight's Arm and Hammer Double Duty®, non-clumping litter, and Clorox's Freshstep® clumping litter). Catsan® litter was purchased at retail in the United Kingdom.

A. Test Protocol

1. Ammonia Test

Odor control properties of cat litters were determined against diluted ammonia solution (0.6 wt %). A half cup of cat litter was placed into a 1.25 L glass vessel; each vessel sealed with plastic film. On a daily basis, 1 ml ammonia solution was applied onto half cup of cat litter to simulate 10 lb cat deposits 180 ml urine in the entire box. After applying the ammonia solution for 5 minutes and 24 hours, respectively, ammonia content in the headspace of each carrier vessel was determined using ammonia test meter. Repeat those tests up to 10 days without cat litter replacement.

2. Hydrogen Sulfide Test

Odor control properties of cat litters were determined against diluted hydrogen sulfide solution (lab made). Half cup of cat litter was placed into a 1.25 L glass vessel; each vessel will be sealed with plastic film. 5 ml $H_2S$ solution was applied onto each cat litter. After applying the $H_2S$ solution for 2, 30 and 60 minutes respectively, $H_2S$ content in the headspace of each carrier vessel was determined using $H_2S$ test meter.

B. Test Results

Figure 2:
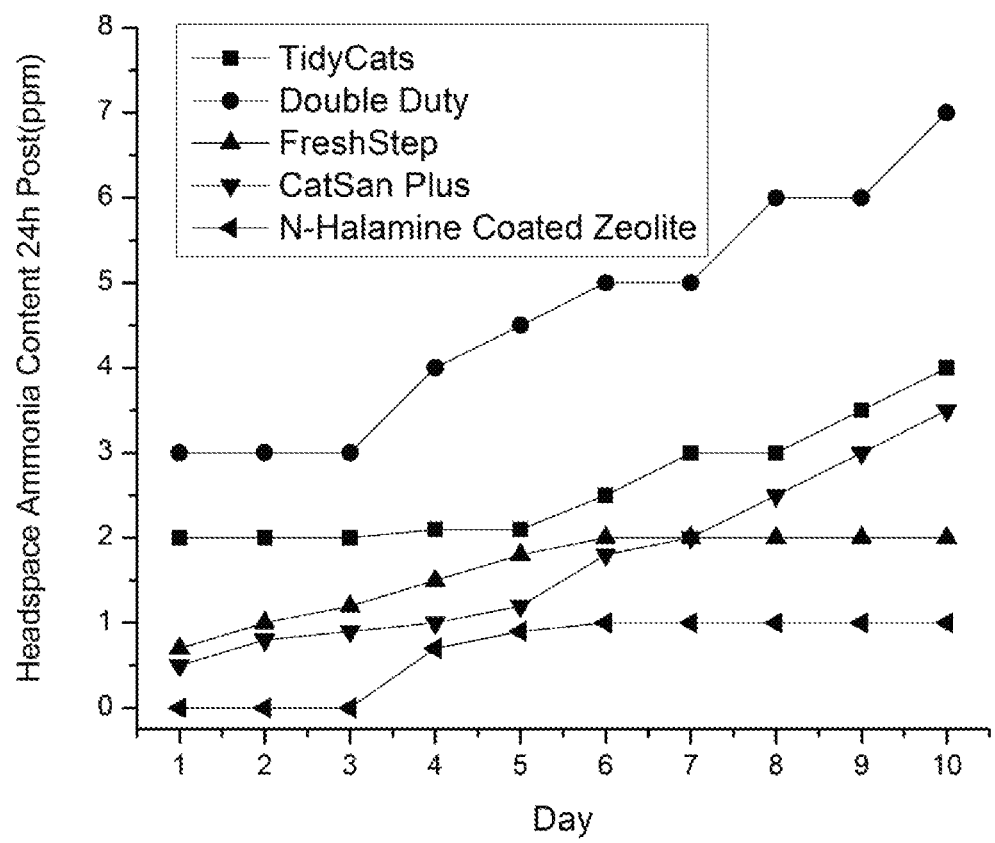
FIG. 2 is a graph showing 24 hour headspace ammonia content over litter samples spiked with ammonia solution daily to simulate the total urinary output of one cat per day in a worst case scenario in which all the urea in the urine is converted to ammonia.
Figure 3:
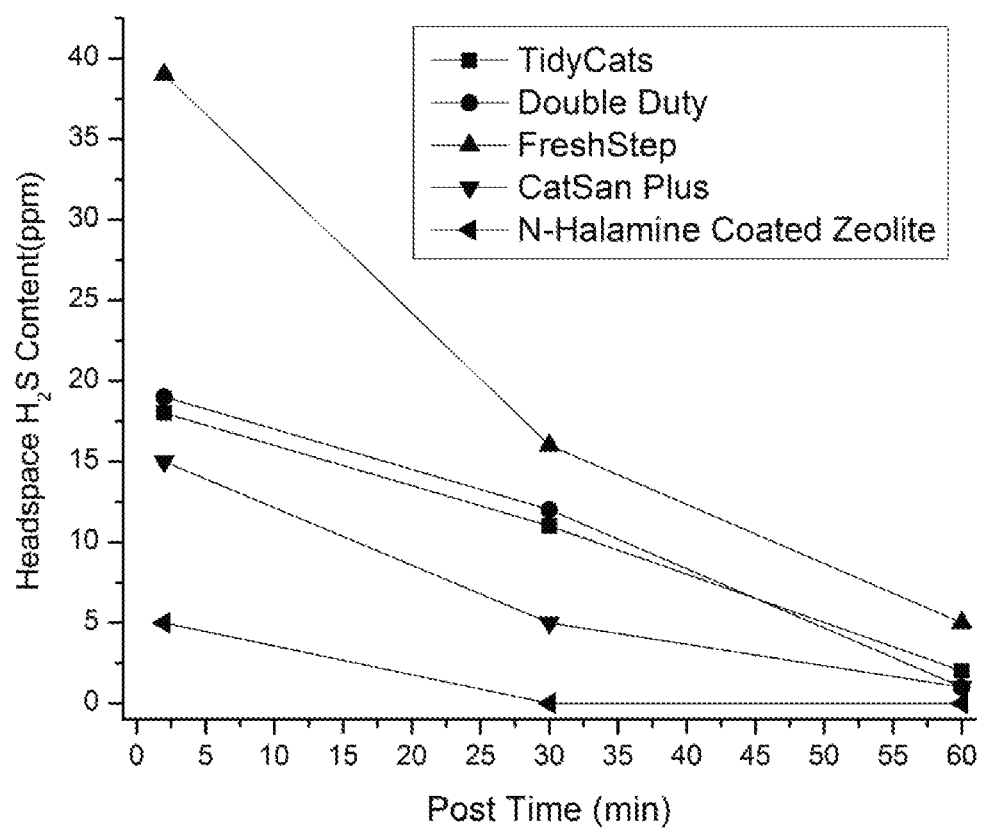
FIG. 3 is graph showing headspace hydrogen sulfide content over time after applying hydrogen sulfide solution to test litter samples in amounts that simulate the emanation of hydrogen sulfide from formed stools.

In all tests it was shown (FIGS. 1, 2 and 3) that the degree of odor control of both ammonia and $H_2S$ was superior in the N-halamine coated zeolite formulation compared to all other commercially available odor control cat litters. In these experiments the coating applied to the zeolite contained 0.25 wt % MCDMH. Although these formulations contain disinfecting functionality, the speed with which the malodorous compounds were affected in these tests is not compatible the results being due to antimicrobial properties of the coating. Also, although the coatings have a demonstrable enzyme-inhibiting component (MCDMH) the results in these experiments are not compatible with the odor control being due to inhibition of urease or any other malodor generating enzymes. In real life where microbial contamination is capable of generating malodors it is possible that both these mechanisms may contribute to odor abatement. The results suggest that the zeolite coatings may bring about odor control by direct oxidative degradation of malodors, as well as from antimicrobial and anti-enzyme efficacies that have been demonstrated in prior examples.

Example 17

In these experiments the efficacy of the N-halamine coated zeolite was evaluated as a topping layer applied to soiled cat litter boxes, as an example of soiled animal bedding. The purpose was to demonstrate the utility of a novel mode of odor control brought about by layering the multifunctional deodorizing particulate medium over soiled conventional litter beds. In four households in which cats were resident and which used cat litter boxes containing conventional litter, the N-halamine coated zeolite was layered about ½ inch thick over the soiled substrate. Observations on the degree and speed of impact on the odor emanating from the litter boxes were made by six observers in total. All reported noticeable reduction in urine and fecal malodors within minutes of applying the topping layer. The results suggest that a multifunctional topping layer can be a useful means of reducing soiled animal litter odors, and that the speed of the efficacy demonstrated indicates at least some of this effect is due to direct oxidative degradation of malodor molecules.

What is claimed is:

1. A method for preparing an antimicrobial and/or deodorizing and/or enzyme inactivating material by applying a water-based disinfecting and deodorizing fluid to a substrate of said material and allowing the fluid to dry on said substrate to create the antimicrobial and/or deodorizing and/or enzyme inactivating material, wherein the water-based disinfecting and deodorizing fluid is comprised of (a) at least N-halamine, wherein the N-halamine is selected from the group consisting of N-chloro-N-sodiomethylbenzenesulfonamidate trihydrate, N,N-dichloro-4-methylbenzenesulfonamide, N-bromo-N-sodio-4-nitrobenzenesulfonamidate, N,N-dichlorobenzenesulfonamide, N-chloro-N-sodiobenzenesulfonamidate, mono-chlorosulfamate, dichlorosulfamate, N-chloroimidodisulfonates, sodium N-chloro-N-arylsulfamates, 2,4,6,8-tetrachloro-2,4,6,8-tetrazobicyclooctane-3,7-dione, sodium trichloroimidometaphosphamate, N-halosulfinylamines, N-halo-N-sodioamidates, chloroisocyanurates, N-halocarbamidates, N-halosulfonamidates, N-chloro-imidodisulfonate, N,N-dichloromethylamine, 2-chloro-1,3,5-triazine-2,4,6-triamine, 2,4-dichloro-1,3,5-triazine-2,4,6-triamine, 2,4,6-trichloro-1, 3,5-triazine-2,4,6-triamine, 1-chloro-5,5-dimethylhydantoin, 1-bromo-5,5-dimethylhydantoin, 1,3-dibromo-5,5-dimethylhydantoin 1-chloro-3-bromo-5,5-dimethylhydantoin, 1,3-dichloro-5,5-dimethylhydantoin, 1-chloro-4,4,5,5-tetramethylimidazolidin-2-one, 1,3-dichloro-4,4,5,5-tetramethylimidazolidin-2-one, 1-chloro-2,2,5,5-tetramethylimidazolidin-4-one, 1,3-dichloro-2,2,5,5-tetramethylimidazolidin-4-one, 1,3-dichloro-s-triazine-2,4, 6-trione, trichloroisocyanuric acid, potassium dichloroisocyanurate, sodium dichloroisocyanurate, potassium dibromoisocyanurate, sodium dibromoisocyanurate, mono to hexachloromelamine, mono to hexabromomelamine, 3-chloro-4,4-dimethyl-2-oxazolidinone, N-chlorosuccinimide, 1-chloropyrrolidine-2,5-dione, 1,3-dichlorotetrahydroquinazoline-2,4-dione, 1,4-dichloro-2,2,5, 5-tetrasubstituted-piperazine-3,6-diones, N-chloro-2,2,6,6-tetramethylpiperidine, N-chloro-4-amino-2,2,6,6-tetramethylpiperidine, polymer-bound N-chloro-N-sodiobenzenesulfonamidates, chlorinated polyacrylamide, brominated polyacrylamide, chlorinated poly(methacrylamide), brominated poly(methacrylamide), poly(N-chloro-2,2, 6,6-tetramethyl-4-piperidinyl acrylate), poly(N-chloro-hydantoin-methyl-p-styrene) emulsion, 1-chloro-3-bromoalkyltrimethylammonium-4,4,5,5-tetramethyl imidazolidin-2-one, 1-bromo-3-bromoalkyltrimethylammonium-4,4,5,5-tetramethyl imidazolidin-2-one, 1-chloro-3-bromoalkyltrimethylammonium-2,2,5,5-tetramethyl imidazolidin-4-one, 1-bromo-3-bromoalkyltrimethylammonium-2,2,5,5-tetramethyl imidazolidin-4-one, 2-chloro-4-bromoalkyltrimethylammonium-1,3,5-triazine-2,4,6-triamine, 2-bromo-4-bromoalkyltrimethylammonium-1,3,5-triazine-2,4,6-triamine, 1-chloro-3-bromoalkyltrimethylammonium-5,5-dimethylhydantoin, and 1 bromo-3-bromoalkyltrimethylammonium-5,5-dimethylhydantoin; and (b) at least one halogen stabilizing compound or at least one polymeric binder/stabilizing agent, wherein the halogen stabilizing compound is selected from the group consisting of hydroquinone, 2,2,5,5-tetramethylimidazolidine-4-one, (2,2,6,6-tetramethylpiperidin-1-yl) oxy, 2,2,6,6-tetramethyl-piperidine-1,4-diol, 2,2,6,6-tetramethyl-4-piperidinol, 4-amino-2,2,6,6-tetramethylpiperidine, 2,2,6,6-tetramethylpiperidine, 2,2,6,6-tetramethyl-4-piperidyl methacrylate, 2,2,6,6-tetramethyl-4-piperidone, (2,2,6, 6-tetramethylpiperidin-4-yl) benzoate, 1,1'-ethylenebis(3,3, 5,5-tetramethylpiperazinone), 4-acetamido-2,2,6,6-tetramethylpiperidine, bis(2,2,6,6-tetramethyl-4-piperidyl)

succinate, bis(2,2,6,6-tetramethylpiperidin-4-yl) butanedioate, bis(2,2,6,6-tetramethylpiperidin-4-yl)hexane-1,6-diamine, and wherein the polymeric binder/stabilizing agent is selected from the group consisting of cellulose, carboxylic cellulose, carboxymethyl cellulose, hydroxyethyl cellulose, hydroxypropyl cellulose, starch, guar gum, gelatin, vinyl resin emulsion, acrylic resin emulsion, polyacrylamide, poly(methacrylamide), polyacrylic acid, polyethyleneimine, poly(vinyl alcohol), poly(vinylpyrrolidinone), poly(ethylene glycol), poly(ethylene oxide), poly(N-isopropylacrylamide), poly(2-oxazoline), poly(allylamine hydrochloride), poly(styrenesulfonate), and poly(diallyldimethylammonium chloride).

2. The method as specified in claim 1 wherein the water-based disinfecting and deodorizing fluid includes at least one of both the halogen stabilizing compounds and at least one of the the polymeric binder/stabilizing agents.

3. The method as specified in claim 1 wherein the material is a woven textile material or a nonwoven textile material.

4. The method as specified in claim 2 wherein the material is a woven textile material or a nonwoven textile material.

5. The method as specified in claim 1 wherein the material is solid material.

6. The method as specified in claim 2 wherein the material is solid material.

7. The method as specified in claim 1 wherein the material is a particulate material, wherein the particulate material is inorganic or organic, wherein the particulate material is porous or non-porous, and wherein the particulate material is natural or synthetic.

8. The method as specified in claim 2 wherein the material is a particulate material, wherein the particulate material is inorganic or organic, wherein the particulate material is porous or non-porous, and wherein the particulate material is natural or synthetic.

9. The method as specified in claim 1 wherein the material is a porous material.

10. The method as specified in claim 9 wherein the material is a sponge or foam or granular medium.

11. The method as specified in claim 2 wherein the material is a porous material.

12. The method as specified in claim 11 wherein the material is a sponge or foam or granular medium.

13. A method for disinfecting and/or deodorizing an area of skin on a human or an animal which comprises applying a water-based disinfecting and deodorizing fluid to the area of skin on the human or the animal, wherein the water-based disinfecting and deodorizing fluid is comprised of (a) at least one N-halamine, wherein the N-halamine is selected from the group consisting of N-chloro-N-sodiomethylbenzenesulfonamidate trihydrate, N,N-dichloro-4-methylbenzenesulfonamide, N-bromo-N-sodio-4-nitrobenzenesulfonamidate, N,N-dichlorobenzenesulfonamide, N-chloro-N-sodiobenzenesulfonamidate, mono-chlorosulfamate, dichlorosulfamate, N-chloroimidodisulfonates, sodium N-chloro-N-arylsulfamates, 2,4,6,8-tetrachloro-2,4,6,8-tetrazobicyclooctane-3,7-dione, sodium trichloroimidometaphosphamate, N-halosulfinylamines, N-halo-N-sodioamidates, chloroisocyanurates, N-halocarbamidates, N-halosulfonamidates, N-chloro-imidodisulfonate, N,N-dichloromethylamine, 2-chloro-1,3,5-triazine-2,4,6-triamine, 2,4-dichloro-1,3,5-triazine-2,4,6-triamine, 2,4,6-trichloro-1,3,5-triazine-2,4,6-triamine, 1-chloro-5,5-dimethylhydantoin, 1-bromo-5,5-dimethylhydantoin, 1,3-dibromo-5,5-dimethylhydantoin 1-chloro-3-bromo-5,5-dimethylhydantoin, 1,3-dichloro-5,5-dimethylhydantoin, 1-chloro-4,4,5,5-tetramethylimidazolidin-2-one, 1,3-dichloro-4,4,5,5-tetramethylimidazolidin-2-one, 1-chloro-2,2,5,5-tetramethylimidazolidin-4-one, 1,3-dichloro-2,2,5,5-tetramethylimidazolidin-4-one, 1,3-dichloro-s-triazine-2,4,6-trione, trichloroisocyanuric acid, potassium dichloroisocyanurate, sodium dichloroisocyanurate, potassium dibromoisocyanurate, sodium dibromoisocyanurate, mono to hexachloromelamine, mono to hexabromomelamine, 3-chloro-4,4-dimethyl-2-oxazolidinone, N-chlorosuccinimide, 1-chloropyrrolidine-2,5-dione, 1,3-dichlorotetrahydroquinazoline-2,4-dione, 1,4-dichloro-2,2,5,5-tetrasubstituted-piperazine-3,6-diones, N-chloro-2,2,6,6-tetramethylpiperidine, N-chloro-4-amino-2,2,6,6-tetramethylpiperidine, polymer-bound N-chloro-N-sodiobenzenesulfonamidates, chlorinated polyacrylamide, brominated polyacrylamide, chlorinated poly(methacrylamide), brominated poly(methacrylamide), poly(N-chloro-2,2,6,6-tetramethyl-4-piperidinyl acrylate), poly(N-chloro-hydantoin-methyl-p-styrene) emulsion, 1-chloro-3-bromoalkyltrimethylammonium-4,4,5,5-tetramethyl imidazolidin-2-one, 1-bromo-3-bromoalkyltrimethylammonium-4,4,5,5-tetramethyl imidazolidin-2-one, 1-chloro-3-bromoalkyltrimethylammonium-2,2,5,5-tetramethyl imidazolidin-4-one, 1-bromo-3-bromoalkyltrimethylammonium-2,2,5,5-tetramethyl imidazolidin-4-one, 2-chloro-4-bromoalkyltrimethylammonium-1,3,5-triazine-2,4,6-triamine, 2-bromo-4-bromoalkyltrimethylammonium-1,3,5-triazine-2,4,6-triamine, 1-chloro-3-bromoalkyltrimethylammonium-5,5-dimethylhydantoin, and 1 bromo-3-bromoalkyltrimethylammonium-5,5-dimethylhydantoin; and (b) at least one halogen stabilizing compound or at least one polymeric binder/stabilizing agent, wherein the halogen stabilizing compound is selected from the group consisting of hydroquinone, 2,2,5,5-tetramethylimidazolidine-4-one, (2,2,6,6-tetramethylpiperidin-1-yl) oxy, 2,2,6,6-tetramethyl-piperidine-1,4-diol, 2,2,6,6-tetramethyl-4-piperidinol, 4-amino-2,2,6,6-tetramethylpiperidine, 2,2,6,6-tetramethylpiperidine, 2,2,6,6-tetramethyl-4-piperidyl methacrylate, 2,2,6,6-tetramethyl-4-piperidone, (2,2,6,6-tetramethylpiperidin-4-yl) benzoate, 1,1'-ethylenebis(3,3,5,5-tetramethylpiperazinone), 4-acetamido-2,2,6,6-tetramethylpiperidine, bis(2,2,6,6-tetramethyl-4-piperidyl) succinate, bis(2,2,6,6-tetramethylpiperidin-4-yl) butanedioate, bis(2,2,6,6-tetramethylpiperidin-4-yl)hexane-1,6-diamine, and wherein the polymeric binder/stabilizing agent is selected from the group consisting of cellulose, carboxylic cellulose, carboxymethyl cellulose, hydroxyethyl cellulose, hydroxypropyl cellulose, starch, guar gum, gelatin, vinyl resin emulsion, acrylic resin emulsion, polyacrylamide, poly(methacrylamide), polyacrylic acid, polyethyleneimine, poly(vinyl alcohol), poly(vinylpyrrolidinone), poly(ethylene glycol), poly(ethylene oxide), poly(N-isopropylacrylamide), poly(2-oxazoline), poly(allylamine hydrochloride), poly(styrenesulfonate), and poly(diallyldimethylammonium chloride).

14. The method as specified in claim 13 wherein the water-based disinfecting and deodorizing fluid includes at least one of the halogen stabilizing compounds and at least one of the one water soluble/dispersible polymeric binder/stabilizing agents.

15. The method for disinfecting and/or deodorizing the surface of equipment for use in food processing, agricultural, or industrial processes which comprises applying a water-based disinfecting and deodorizing fluid to the surface of said equipment, wherein the water-based disinfecting and deodorizing fluid is comprised of (a) at least one N-halamine, wherein the N-halamine is selected from the group consisting of N-chloro-N-sodiomethylbenzenesulfonamidate trihydrate, N,N-dichloro-4-methylbenzenesulfonamide, N-bromo-N-sodio-4-nitrobenzenesulfonamidate, N,N-dichlorobenzenesulfonamide, N-chloro-N-sodiobenzenesulfonamidate, mono-chlorosulfamate, dichlorosulfamate, N-chloroimidodisulfonates, sodium N-chloro-N-arylsulfamates, 2,4,6,8-tetrachloro-2,4,6,8-tetrazobicyclooctane-3,7-dione, sodium trichloroimidometaphosphamate, N-halosulfinylamines, N-halo-N-sodioamidates, chloroisocyanurates, N-halocarbamidates, N-halosulfonamidates, N-chloro-imidodisulfonate, N,N-dichloromethylamine, 2-chloro-1,3,5-triazine-2,4,6-triamine, 2,4-dichloro-1,3,5-triazine-2,4,6-triamine, 2,4,6-trichloro-1,3,5-triazine-2,4,6-triamine, 1-chloro-5,5-dimethylhydantoin, 1-bromo-5,5-dimethylhydantoin, 1,3-dibromo-5,5-dimethylhydantoin 1-chloro-3-bromo-5,5-dimethylhydantoin, 1,3-dichloro-5,5-dimethylhydantoin, 1-chloro-4,4,5,5-tetramethylimidazolidin-2-one, 1,3-dichloro-4,4,5,5-tetramethylimidazolidin-2-one, 1-chloro-2,2,5,5-tetramethylimidazolidin-4-one, 1,3-dichloro-2,2,5,5-tetramethylimidazolidin-4-one, 1,3-dichloro-s-triazine-2,4,6-trione, trichloroisocyanuric acid, potassium dichloroisocyanurate, sodium dichloroisocyanurate, potassium dibromoisocyanurate, sodium dibromoisocyanurate, mono to hexachloromelamine, mono to hexabromomelamine, 3-chloro-4,4-dimethyl-2-oxazolidinone, N-chlorosuccinimide, 1-chloropyrrolidine-2,5-dione, 1,3-dichlorotetrahydroquinazoline-2,4-dione, 1,4-dichloro-2,2,5,5-tetrasubstituted-piperazine-3,6-diones, N-chloro-2,2,6,6-tetramethylpiperidine, N-chloro-4-amino-2,2,6,6-tetramethylpiperidine, polymer-bound N-chloro-N-sodiobenzenesulfonamidates, chlorinated polyacrylamide, brominated polyacrylamide, chlorinated poly(methacrylamide), brominated poly(methacrylamide), poly(N-chloro-2,2,6,6-tetramethyl-4-piperidinyl acrylate), poly(N-chloro-hydantoin-methyl-p-styrene) emulsion, 1-chloro-3-bromoalkyltrimethylammonium-4,4,5,5-tetramethyl imidazolidin-2-one, 1-bromo-3-bromoalkyltrimethylammonium-4,4,5,5-tetramethyl imidazolidin-2-one, 1-chloro-3-bromoalkyltrimethylammonium-2,2,5,5-tetramethyl imidazolidin-4-one, 1-bromo-3-bromoalkyltrimethylammonium-2,2,5,5-tetramethyl imidazolidin-4-one, 2-chloro-4-bromoalkyltrimethylammonium-1,3,5-triazine-2,4,6-triamine, 2-bromo-4-bromoalkyltrimethylammonium-1,3,5-triazine-2,4,6-triamine, 1-chloro-3-bromoalkyltrimethylammonium-5,5-dimethylhydantoin, and 1 bromo-3-bromoalkyltrimethylammonium-5,5-dimethylhydantoin; and (b) at least halogen stabilizing compound or at least one polymeric binder/stabilizing agent, wherein the halogen stabilizing compound is selected from the group consisting of hydroquinone, 2,2,5,5-tetramethylimidazolidine-4-one, (2,2,6,6-tetramethylpiperidin-1-yl)oxy, 2,2,6,6-tetramethyl-piperidine-1,4-diol, 2,2,6,6-tetramethyl-4-piperidinol, 4-amino-2,2,6,6-tetramethylpiperidine, 2,2,6,6-tetramethylpiperidine, 2,2,6,6-tetramethyl-4-piperidyl methacrylate, 2,2,6,6-tetramethyl-4-piperidone, (2,2,6,6-tetramethylpiperidin-4-yl) benzoate, 1,1'-ethylenebis(3,3,5,5-tetramethylpiperazinone), 4-acetamido-2,2,6,6-tetramethylpiperidine, bis(2,2,6,6-tetramethyl-4-piperidyl) succinate, bis(2,2,6,6-tetramethylpiperidin-4-yl) butanedioate, and bis (2,2,6,6-tetramethylpiperidin-4-yl)hexane-1,6-diamine, and wherein the polymeric binder/stabilizing agent is selected from the group consisting of cellulose, carboxylic cellulose, carboxymethyl cellulose, hydroxyethyl cellulose, hydroxypropyl cellulose, starch, guar gum, gelatin, vinyl resin emulsion, acrylic resin emulsion, polyacrylamide, poly(methacrylamide), polyacrylic acid, polyethyleneimine, poly(vinyl alcohol), poly(vinylpyrrolidinone), poly(ethylene glycol), poly(ethylene oxide), poly(N-isopropylacrylamide), poly(2-oxazoline), poly(allylamine hydrochloride), poly(styrenesulfonate), and poly(diallyldimethylammonium chloride).

16. The method as specified in claim 15 wherein the water-based disinfecting and deodorizing fluid includes at least one of the halogen stabilizing compounds and at least one of the polymeric binder/stabilizing agents.

17. The method as specified in claim 1 wherein the N-halamine is present in the water-based disinfecting and deodorizing fluid at a level which is within the range of 0.01 weight percent to 2 weight percent, based upon the total weight of the water-based disinfecting and deodorizing fluid.

18. The method as specified in claim 1 wherein the N-halamine is present in the water-based disinfecting and deodorizing fluid at a level which is within the range of 0.1 weight percent to 1 weight percent, based upon the total weight of the water-based disinfecting and deodorizing fluid.

19. The method as specified in claim 1 wherein the N-halamine is present in the water-based disinfecting and deodorizing fluid at a level which is within the range of 0.2 weight percent to 0.5 weight percent, based upon the total weight of the water-based disinfecting and deodorizing fluid.

\* \* \* \* \*